(12) United States Patent
Hayami et al.

(10) Patent No.: US 11,145,053 B2
(45) Date of Patent: Oct. 12, 2021

(54) IMAGE PROCESSING APPARATUS AND COMPUTER-READABLE STORAGE MEDIUM STORING INSTRUCTIONS FOR SPECIFYING LESION PORTION AND PERFORMING DIFFERENTIATION CLASSIFICATION IN RESPONSE TO JUDGING THAT DIFFERENTIATION CLASSIFICATION OPERATION IS ENGAGED BASED ON SIGNAL FROM ENDOSCOPE

(71) Applicant: OLYMPUS CORPORATION, Tokyo (JP)

(72) Inventors: Takehito Hayami, Tokyo (JP); Yamato Kanda, Tokyo (JP); Takashi Kono, Tokyo (JP); Mitsutaka Kimura, Tokyo (JP); Ryoji Takami, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 81 days.

(21) Appl. No.: 16/433,483

(22) Filed: Jun. 6, 2019

(65) Prior Publication Data
US 2019/0311476 A1   Oct. 10, 2019

Related U.S. Application Data

(63) Continuation of application No. PCT/JP2016/086409, filed on Dec. 7, 2016.

(51) Int. Cl.
*G06T 7/00* (2017.01)
*G06T 7/11* (2017.01)
(Continued)

(52) U.S. Cl.
CPC .............. *G06T 7/0012* (2013.01); *A61B 1/00* (2013.01); *A61B 1/00009* (2013.01); *A61B 1/04* (2013.01);
(Continued)

(58) Field of Classification Search
CPC ... A61B 1/00; A61B 1/00006; A61B 1/00009; A61B 1/00045; A61B 1/04; A61B 1/05;
(Continued)

(56) References Cited

U.S. PATENT DOCUMENTS 8,542,896 B2* 9/2013 Tanaka .................. G06T 7/0012
382/128
2004/0059215 A1 3/2004 Nishimura et al.
(Continued)

FOREIGN PATENT DOCUMENTS

CN 106102556 A 11/2016
CN 107708521 A 2/2018
(Continued)

*Primary Examiner* — Menatoallah Youssef
(74) *Attorney, Agent, or Firm* — Scully, Scott, Murphy & Presser, P.C.

(57) ABSTRACT

An image processing apparatus have a processor configured to: receive a plurality of images of a tissue including a lesion portion, the plurality of images being received from an endoscope; judge, based on a signal from the endoscope, whether or not to engage a differentiation classification operation; in response to judging that the differentiation classification operation is engaged, process the plurality of images to specify the lesion portion within one or more of the plurality of images; and perform differentiation classification on the one or more images to classify the lesion portion into at least one class of a plurality of classes; and in response to judging that the differentiation classification
(Continued)

operation is not engaged, not process the plurality of images to specify the lesion portion within the one or more of the plurality of images.

14 Claims, 16 Drawing Sheets

(51) Int. Cl.

| | | |
|---|---|---|
| *G06T 7/70* | (2017.01) | |
| *A61B 1/00* | (2006.01) | |
| *A61B 1/06* | (2006.01) | |
| *A61B 1/31* | (2006.01) | |
| *A61B 5/00* | (2006.01) | |
| *G06F 3/01* | (2006.01) | |
| *G06K 9/62* | (2006.01) | |
| *G06T 7/20* | (2017.01) | |
| *G06T 7/60* | (2017.01) | |
| *H04N 5/225* | (2006.01) | |
| *A61B 1/04* | (2006.01) | |

(52) U.S. Cl.
CPC .............. *A61B 1/0638* (2013.01); *A61B 1/31* (2013.01); *A61B 5/489* (2013.01); *A61B 5/7264* (2013.01); *G06F 3/013* (2013.01); *G06K 9/628* (2013.01); *G06T 7/11* (2017.01); *G06T 7/20* (2013.01); *G06T 7/60* (2013.01); *G06T 7/70* (2017.01); *H04N 5/2256* (2013.01); *G06K 2209/05* (2013.01); *G06T 2207/10068* (2013.01); *G06T 2207/10152* (2013.01); *G06T 2207/30028* (2013.01); *G06T 2207/30092* (2013.01); *G06T 2207/30096* (2013.01); *G06T 2207/30101* (2013.01); *G06T 2207/30244* (2013.01); *H04N 2005/2255* (2013.01)

(58) Field of Classification Search
CPC ......... A61B 1/0638; A61B 1/31; A61B 5/489; A61B 5/7264; G06F 3/013; G06K 2209/05; G06K 9/4604; G06K 9/4671; G06K 9/6269; G06K 9/628; G06T 2207/10068; G06T 2207/10152; G06T 2207/30028; G06T 2207/30092; G06T 2207/30096; G06T 2207/30101; G06T 2207/30244; G06T 7/0012; G06T 7/11; G06T 7/20; G06T 7/60; G06T 7/70; H04N 2005/2255; H04N 5/2256
See application file for complete search history.

(56) References Cited

U.S. PATENT DOCUMENTS

| | | | |
|---|---|---|---|
| 2009/0074268 A1 | 3/2009 | Tanaka et al. | |
| 2010/0063355 A1 | 3/2010 | Matsuura | |
| 2014/0028821 A1 | 1/2014 | Tanaka et al. | |
| 2016/0134824 A1* | 5/2016 | Gomi | H04N 5/378 348/76 |
| 2018/0114319 A1 | 4/2018 | Kono et al. | |
| 2018/0153384 A1* | 6/2018 | Ikemoto | G06T 5/002 |

FOREIGN PATENT DOCUMENTS

| | | |
|---|---|---|
| EP | 1 452 129 A1 | 9/2004 |
| JP | H01-101965 A | 4/1989 |
| JP | 2003-126045 A | 5/2003 |
| JP | 2007-244518 A | 9/2007 |
| JP | 2010-063589 A | 3/2010 |
| JP | 2010-075368 A | 4/2010 |
| JP | 2011-255006 A | 12/2011 |
| JP | 2012-071007 A | 4/2012 |
| JP | 2012-152332 A | 8/2012 |
| JP | 2012-239815 A | 12/2012 |
| JP | 2016-158682 A | 9/2016 |
| WO | 03/034914 A1 | 5/2003 |
| WO | 2013/140667 A1 | 9/2013 |
| WO | 2015/146836 A1 | 10/2015 |
| WO | 2016/136700 A1 | 9/2016 |

* cited by examiner

IMAGE PROCESSING APPARATUS AND COMPUTER-READABLE STORAGE MEDIUM STORING INSTRUCTIONS FOR SPECIFYING LESION PORTION AND PERFORMING DIFFERENTIATION CLASSIFICATION IN RESPONSE TO JUDGING THAT DIFFERENTIATION CLASSIFICATION OPERATION IS ENGAGED BASED ON SIGNAL FROM ENDOSCOPE

CROSS REFERENCE TO RELATED APPLICATION

This application is a continuation application of PCT/JP2016/086409 filed on Dec. 7, 2016, the entire contents of which are incorporated herein by this reference.

BACKGROUND OF INVENTION

1. Field of the Invention

The present invention relates to an image processing apparatus, and particularly to an image processing apparatus for endoscope inspection.

2. Description of the Related Art

Conventionally, endoscopes have been widely used in medical field, for example. By using an endoscope, an operator can discover and differentiate a lesion portion by looking at an endoscope image within a subject displayed on a display device and further perform treatment using a treatment instrument for the lesion portion, for example.

The operator judges presence or absence of the lesion portion within the subject while looking at the endoscope image displayed on the display device. The operator judges the presence or absence of the lesion portion while moving an insertion section of the endoscope, and makes a distal end portion of the insertion section still when the operator discovers the lesion portion, to differentiate the lesion portion, i.e., specify the disease by looking at the endoscope image.

When the operator desires to differentiate the discovered lesion portion when observing the inside of the subject, the operator may closely observe the endoscope image while subjecting the endoscope image to desired image processing and may display desired feature value information or the like as support information from the result of the image processing.

Japanese Patent Application Laid-Open Publication No. 2010-63589 proposes an endoscope system for detecting an amount of a relative movement between an observation site and a distal end portion of an insertion section and stopping irradiating illumination light for special light observation when the amount of the movement exceeds a predetermined threshold value.

SUMMARY OF THE INVENTION

An aspect of the present invention provides an image processing apparatus comprising a processor comprising hardware, wherein the processor is configured to: receive a plurality of images of a tissue including a lesion portion, the plurality of images being received from an endoscope operated by an operator; judge, based on a signal from the endoscope, whether or not to engage a differentiation classification operation to classify the lesion portion in one or more of the plurality of images; in response to judging that the differentiation classification operation is engaged, process the plurality of images to specify the lesion portion within the one or more of the plurality of images; and perform differentiation classification on the one or more images in which the lesion portion is specified to classify the lesion portion into at least one class of a plurality of classes; and in response to judging that the differentiation classification operation is not engaged, not process the plurality of images to specify the lesion portion within the one or more of the plurality of images.

Another aspect of the present invention provided an image processing apparatus comprising means for receiving a plurality of images of a tissue including a lesion portion, the plurality of images being received from an endoscope operated by an operator; means for judging, based on a signal from the endoscope, whether or not to engage a differentiation classification operation to classify the lesion portion in one or more of the plurality of images; means for, in response to judging that the differentiation classification operation is engaged, processing the plurality of images to specify the lesion portion within the one or more of the plurality of images; and performing differentiation classification on the one or more images in which the lesion portion is specified to classify the lesion portion into at least one class of a plurality of classes; and means for in response to judging that the differentiation classification operation is not engaged, not processing the plurality of images to specify the lesion portion within the one or more of the plurality of images.

Another aspect of the present invention provides a non-transitory computer-readable storage medium storing instructions that cause a computer to at least perform: receiving a plurality of images of a tissue including a lesion portion, the plurality of images being received from an endoscope operated by an operator; judging, based on a signal from the endoscope, whether or not to engage a differentiation classification operation to classify the lesion portion in one or more of the plurality of images; in response to judging that the differentiation classification operation is engaged, processing the plurality of images to specify the lesion portion within the one or more of the plurality of images; and performing differentiation classification on the one or more images in which the lesion portion is specified to classify the lesion portion into at least one class of a plurality of classes; and in response to judging that the differentiation classification operation is not engaged, not processing the plurality of images to specify the lesion portion within the one or more of the plurality of images.

DETAILED DESCRIPTION OF THE PREFERRED EMBODIMENTS

Embodiments of the present invention will be described below with reference to the drawings.

First Embodiment

Figure 1:
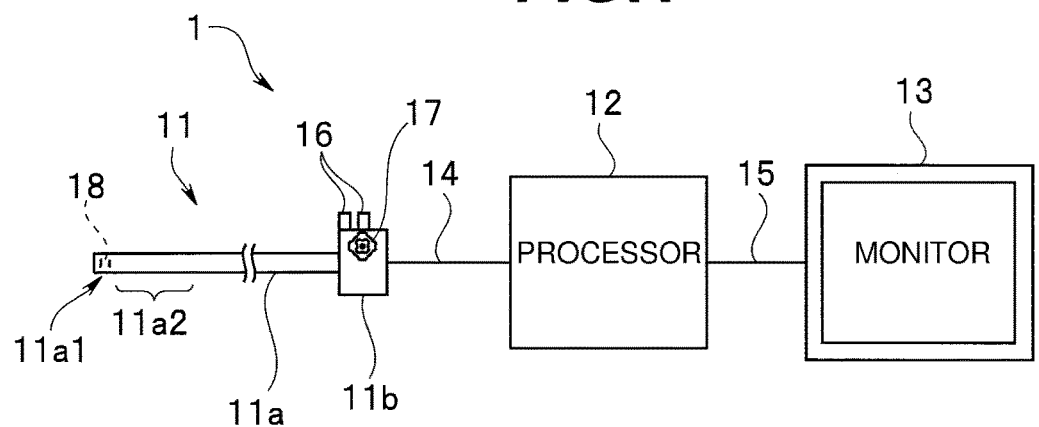
FIG. 1 is a configuration diagram of an endoscope apparatus according to a first embodiment of the present invention.

FIG. 1 is a configuration diagram of an endoscope apparatus according to a first embodiment.

An endoscope apparatus 1 includes an endoscope 11, a video processor 12, and a monitor 13 as a display device. The endoscope 11 and the video processor 12 are connected to each other via a cable 14 such as a universal cable. The video processor 12 and the monitor 13 are connected to each other via a cable 15. The endoscope apparatus 1 has a plurality of observation modes.

The endoscope 11 includes an elongated insertion section 11a and an operation section 11b connected to a proximal end portion of the insertion section 11a. A distal end portion 11a1 of the insertion section 11a is provided with an illumination window and an observation window not illustrated so that illumination light is emitted to a subject from the illumination window and return light from the subject is incident on the observation window. A bending section 11a2 is provided on a proximal end side of the distal end portion 11a1 of the insertion section 11a.

The operation section 11b includes various types of operation buttons 16 such as a freeze button and a bending knob 17 for a bending operation of the bending section 11a2.

An image pickup device 18 is disposed within the distal end portion 11a1 of the insertion section 11a. An object image by light incident from the observation window is photoelectrically converted, to output an image pickup signal. The image pickup signal is fed to the video processor 12 via the cable 14.

The video processor (hereinafter referred to as the processor) 12 as an image processing apparatus includes an image processing circuit, as described below, and generates an endoscope image based on the image pickup signal from the endoscope 11 and outputs an image signal of the endoscope image to the monitor 13 via the cable 15. The endoscope image is displayed on the monitor 13.

The processor 12 includes a light source, and illumination light emitted from the light source is emitted from the illumination window in the distal end portion of the insertion section 11a via the cable 14 and a light guide (not illustrated) inserted into the endoscope 11.

The processor 12 controls the light source and the image processing circuit in response to an observation mode, to generate an endoscope image corresponding to the observation mode set by an operator and output an image signal of the endoscope image to the monitor 13. Accordingly, the endoscope image corresponding to the observation mode is displayed on the monitor 13.

Figure 2:
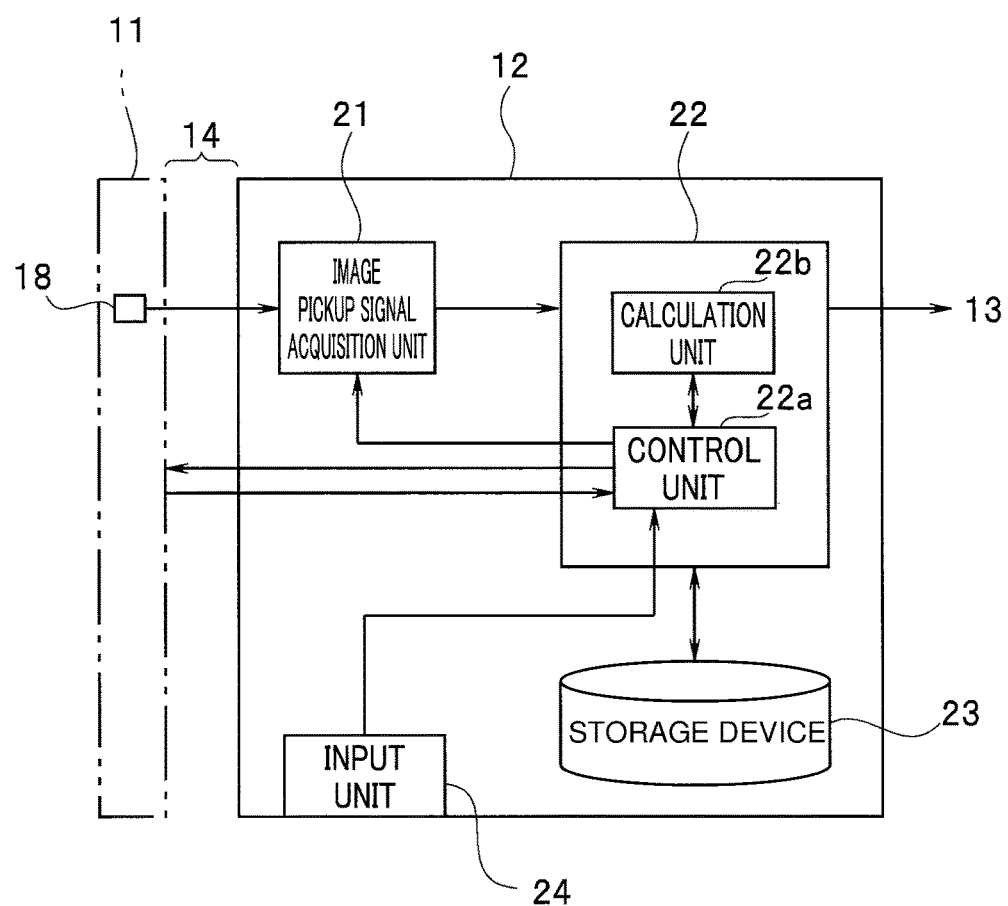
FIG. 2 is a block diagram illustrating a configuration relating to image processing of a processor 12 according to the first embodiment of the present invention.

FIG. 2 is a block diagram illustrating a configuration relating to image processing of the processor 12.

The processor 12 can be an image processing apparatus including an image pickup signal acquisition unit 21, a control calculation unit 22, a storage device 23, and an input unit 24. The control calculation unit 22 includes a central processing unit (hereinafter referred to as a CPU, a ROM, a RAM, and the like reading instructions from a stored software program, or includes a circuit, performing the functions of a control unit 22a and a calculation unit 22b.

The image pickup signal acquisition unit 21 is a circuit configured to receive and acquire the image pickup signal from the image pickup device 18 in the endoscope 11 and output the image pickup signal to the control calculation unit 22 under the control of the control unit 22a.

The control unit 22a, and controls an operation of the entire processor 12 while performing control of driving of the image pickup device 18 in the endoscope 11, control of various types of circuits based on various types of operation signals from the operation section 11b in the endoscope 11, control of recording of various types of data on the storage device 23 and reading of various types of data from the storage device 23, and control of image processing in response to an instruction to the input unit 24 by the operator. Further, the control calculation unit 22 performs control of the light source not illustrated, for example.

In other words, the control unit 22a controls an operation of the endoscope apparatus 1 based on an instruction or an input provided by the input unit 24, to output a control signal or a setting signal to each of the units.

The calculation unit 22b is a circuit configured to perform various types of image processing and various types of calculation processing based on the image pickup signal acquired by the image pickup signal acquisition unit 21 under the control of the control unit 22a while generating the image signal of the endoscope image displayed on the monitor 13 and various types of display information and outputting the image signal and the display information to the monitor 13.

The storage device 23 can be a large-capacity storage device such as a hard disk device, and stores various types of data such as image data of an endoscope image within a subject obtained by endoscope inspection and support information.

The input unit 24 can be an operation panel including various types of buttons and an input device configured for the operator to provide various types of settings and various types of instructions of the endoscope apparatus 1 to the processor 12.

Figure 3A:
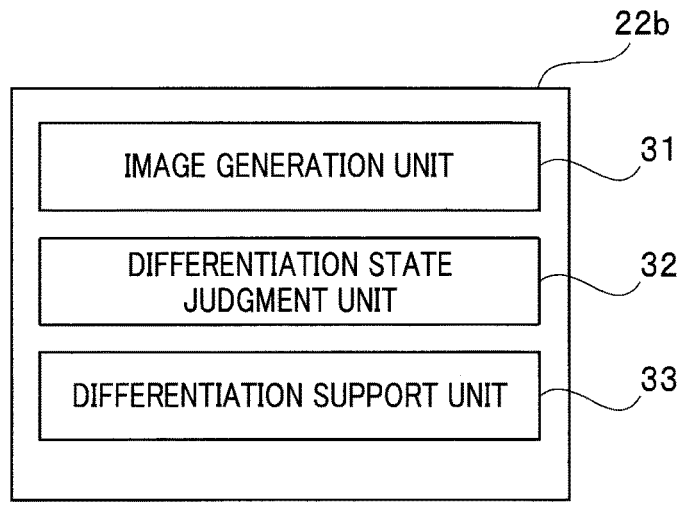
FIG. 3A is a block diagram illustrating a configuration of a calculation unit 22b in a control calculation unit 22 according to the first embodiment of the present invention.

FIG. 3A is a block diagram illustrating a configuration of the calculation unit 22b in the control calculation unit 22.

The calculation unit 22b is a circuit including an image generation unit 31, a differentiation state judgment unit 32, and a differentiation support unit 33.

The image generation unit 31 is a circuit configured to receive an image pickup signal and generate an endoscope image based on the image pickup signal in response to an observation mode. The endoscope apparatus 1 generates, if the observation mode is a normal light observation mode, an endoscope image corresponding to the normal light observation mode, and generates, if the observation mode is a special light observation mode, an endoscope image corresponding to the special light observation mode. Further, the image generation unit 31 performs predetermined emphasis processing, various types of correction processing, and superimposition processing for superimposing and displaying support information, a menu screen, and the like for the endoscope image.

The differentiation state judgment unit 32 is a circuit configured to estimate whether or not the operator is differentiating a lesion portion and judge a differentiation state. In the present embodiment, the differentiation state judgment unit 32 judges that the operator who operates the endoscope 11 is in a differentiation state where a lesion portion in an observation target of the endoscope 11 is being differentiated based on a signal from the endoscope 11.

The differentiation support unit 33 is a circuit configured to perform various types of processing for differentiation support. In other words, the differentiation support unit 33 supports the differentiation of the lesion portion by the operator depending on a judgment result of the differentiation state judgment unit 32.

Figure 3B:
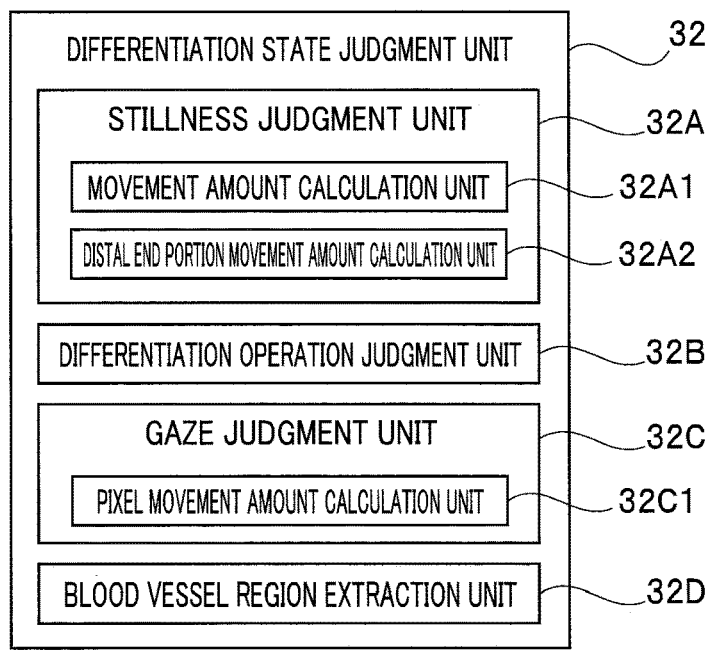
FIG. 3B is a block diagram illustrating a configuration of a differentiation state judgment unit 32 according to the first embodiment of the present invention.
Figure 3C:
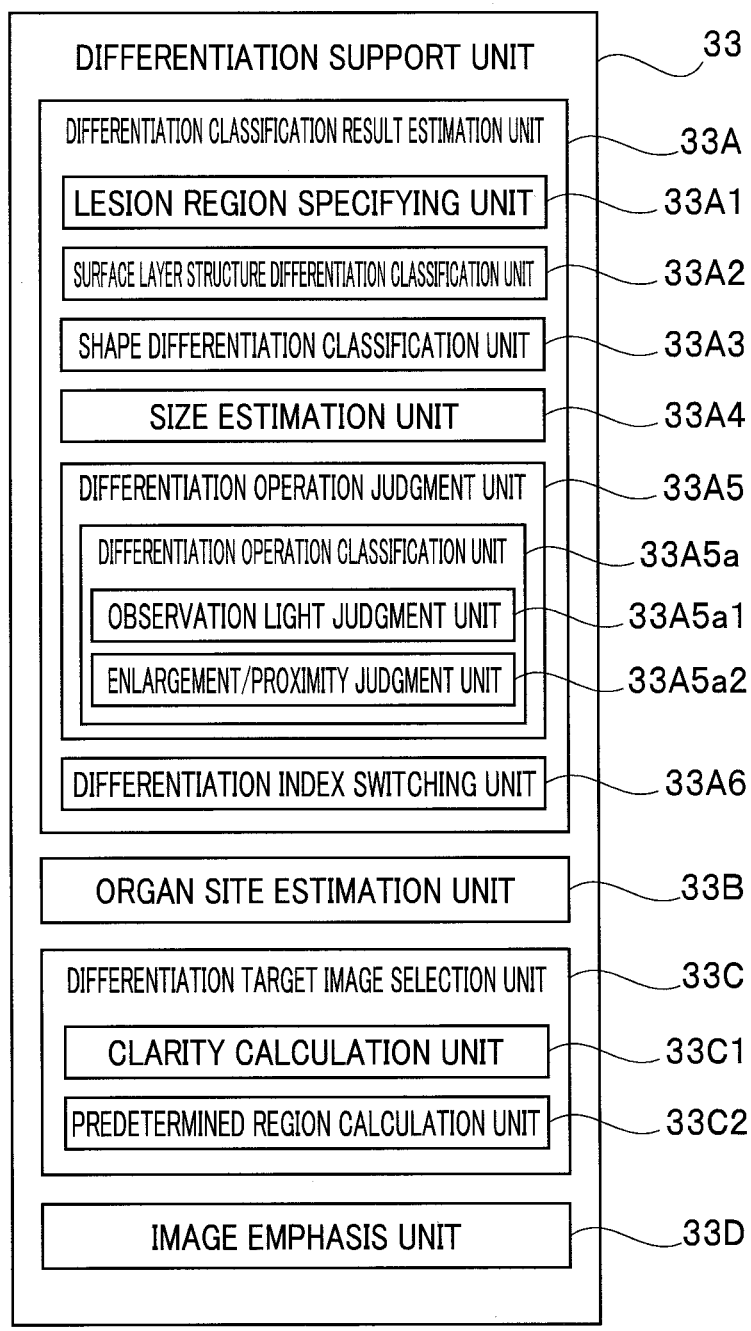
FIG. 3C is a block diagram illustrating a configuration of a differentiation support unit 33 according to the first embodiment of the present invention.

FIG. 3B is a block diagram illustrating a configuration of the differentiation state judgment unit 32. FIG. 3C is a block diagram illustrating a configuration of the differentiation support unit 33.

An operation of each of units in the differentiation state judgment unit 32 and the differentiation support unit 33 illustrated in FIGS. 3B and 3C will be described below in a corresponding part of the following description. FIGS. 3B and 3C illustrate not only a configuration according to the present embodiment described below but also respective configurations according to second and third embodiments and a plurality of modifications described after the present embodiment.

Figure 4:
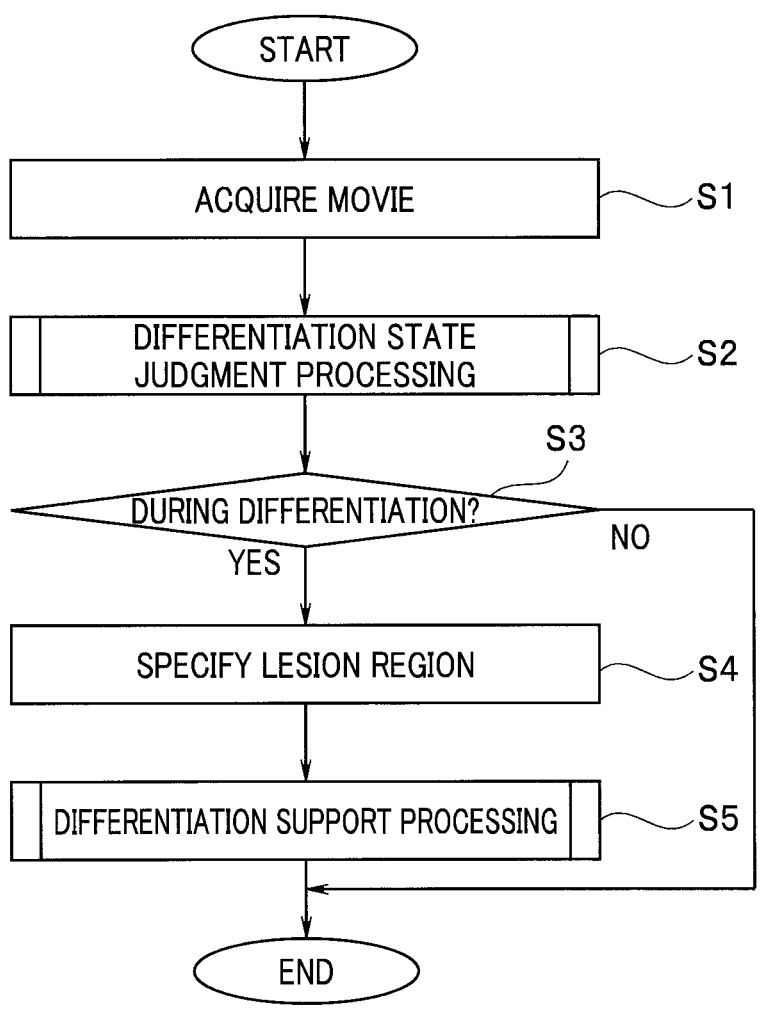
FIG. 4 is a flowchart illustrating an example of a flow of differentiation support processing in a control calculation unit 22 according to the first embodiment of the present invention.

FIG. 4 is a flowchart illustrating an example of a flow of differentiation support processing in the control calculation unit 22. The processing illustrated in FIG. 4 is performed in a predetermined cycle.

When the control unit 22a controls driving of the light source and driving of the image pickup device 18 in the endoscope 11 and controls the image pickup signal acquisition unit 21 in response to a set observation mode, the calculation unit 22b acquires an image pickup signal from the endoscope 11. The image generation unit 31 in the calculation unit 22b generates an endoscope image of a movie having a predetermined frame rate based on the image pickup signal under the control of the control unit 22a.

For example, the processing illustrated in FIG. 4 is performed in a predetermined cycle. The control calculation unit 22 acquires a plurality of frame images, judges whether or not the operator is differentiating the lesion portion, i.e., is performing differentiation based on an image at a time t1 and an image acquired at a time t2 after an elapse of a predetermined time period T from the time t1, and generates support information.

More specifically, the differentiation state judgment unit 32 acquires the endoscope image of the movie generated in the image generation unit 31 (S1).

The differentiation state judgment unit 32 performs differentiation state judgment processing based on the acquired endoscope image (S2).

The differentiation state judgment processing in S2 is to estimate whether or not the operator is differentiating the lesion portion and judge whether or not the operator is performing differentiation.

It is judged whether or not the operator is in a differentiation state based on a movement amount of the whole of the two images extracted at intervals of the predetermined time period T (or frame intervals) from the movie. In other words, respective image pickup regions within the subject in the two images having the intervals of the predetermined time period T therebetween move while the lesion portion is being discovered. However, when the operator is differentiating the lesion portion, the distal end portion 11a1 of the insertion section 11a hardly moves. Accordingly, the two images having the predetermined time intervals therebetween become the same image.

Figure 5:
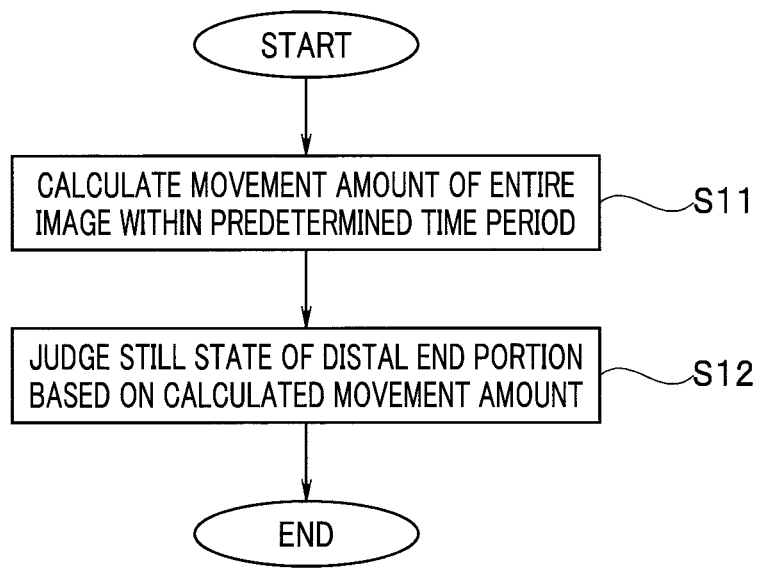
FIG. 5 is a flowchart illustrating an example of a flow of differentiation state judgment processing according to the first embodiment of the present invention.

FIG. 5 is a flowchart illustrating an example of a flow of the differentiation state judgment processing. A movement amount calculation unit 32A1 in a stillness judgment unit 32A in FIG. 3B is associated with the processing illustrated in FIG. 5.

In the present embodiment, the differentiation state judgment processing illustrated in FIG. 5 configures the stillness judgment unit 32A configured to judge whether or not the distal end portion 11a1 of the insertion section 11a in the endoscope 11 remains still based on the endoscope image obtained by the endoscope 11. When it is judged that the distal end portion 11a1 remains still, the differentiation state judgment unit 32 judges that the operator who operates the endoscope 11 is in a differentiation state.

In FIG. 5, the differentiation state judgment unit 32 calculates a movement amount of the entire image based on the two images having the intervals of the predetermined time period T therebetween (S11).

The movement amount of the entire image based on the image at the time t1 and the image at the time t2 after an elapse of the predetermined time period T from the time t1 is calculated from a correlation map by secondary Fourier transform, for example. When it is judged how much a region included in the image at the time t1 has moved in the image at the time t2, the movement amount of the entire image is calculated.

More specifically, frequency information $F_1$ (u, v) and $F_2$ (u, v) are respectively calculated from an image IMG1 at a time t1 and an image IMG2 at a time t2 from the following equation (1). At this time, for the image IMG1, the frequency information is calculated after the image is rotated by 180 degrees.

[Expression 1]

$$F_{1,2}(u, v) = \frac{1}{N}\sum_{x=0}^{N-1}\sum_{y=0}^{N-1} I_{1,2}(x, y)\exp\left\{-\frac{j2\pi(ux + vy)}{N}\right\} \quad (1)$$

$$j = \sqrt{-1}$$

Here, j indicates an imaginary unit, u indicates a spatial frequency in an x direction, v indicates a spatial frequency in a y direction, and N indicates a positive integer.

When a product of the obtained frequency information $F_1$ (u, v) and $F_2$ (u, v) is taken, a correlation map M (x, y) can be created. In the correlation map, a difference between coordinates $(X_M, Y_M)$ at which a correlation value reaches a maximum and center coordinates $(X_C, Y_C)$ of the image is calculated, to obtain a movement amount between the two images.

Note that the movement amount between the images may be calculated by averaging respective movement amounts for feature values obtained by known template matching of the entire image or feature value matching based on an SIFT (scale-invariant feature transform) feature value or the like.

The template matching of the entire image is described in "Digital Image Processing" (revised new edition) published by Computer Graphic Arts Society (CG-ARTS), on page. 218, and the feature point matching based on the SIFT feature value is described in "Digital Image Processing" (revised new edition) published by Computer Graphic Arts Society (CG-ARTS), pp. 234.

After S11, the differentiation state judgment unit 32 judges a still state of the distal end portion 11a1 of the insertion section 11a based on the calculated movement amount of the entire image (S12).

Referring to FIG. 4 again, the differentiation state judgment unit 32 judges whether or not the distal end portion 11a1 of the insertion section 11a remains still, i.e., the lesion portion is being differentiated based on a result of the processing in S2 (S3). In other words, when the distal end portion 11a1 remains still, the differentiation state judgment unit 32 estimates that the operator is differentiating the lesion portion.

The differentiation state judgment unit 32 judges that the operator is differentiating the lesion portion, i.e., the lesion portion is being differentiated when the calculated movement amount of the entire image is a predetermined threshold value TH1 or less, and judges that the lesion portion is not being differentiated when the calculated movement amount of the entire image exceeds the predetermined threshold value TH1.

As described above, the processing in S11 configures an image movement amount calculation unit configured to calculate the movement amount of the entire endoscope image in the predetermined time period T, and the stillness judgment unit 32A judges that the distal end portion 11a1 remains still when the movement amount is less than the predetermined threshold value TH1.

Referring to FIG. 4 again, when the operator is differentiating the lesion portion (S3: YES), the differentiation support unit 33 specifies a lesion region in the lesion portion (S4). Processing in S4 configures a lesion region specifying unit 33A1 configured to specify the lesion region.

The lesion region is specified by polyp candidate detection processing as disclosed in Japanese Patent Application Laid-Open Publication No. 2007-244518, for example. In the above-described example, processing for specifying the lesion region is performed for the image IMG2 at the time t2, for example.

After S4, the differentiation support unit 33 performs the differentiation support processing (S5).

Figure 6:
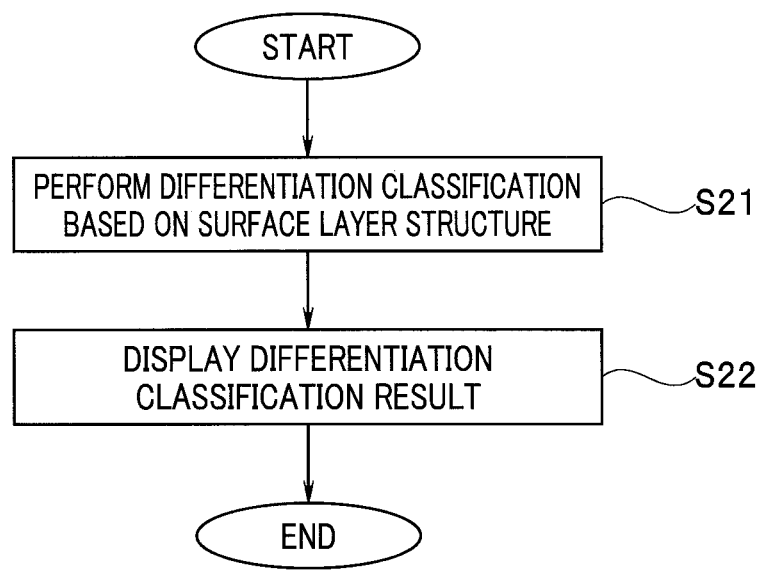
FIG. 6 is a flowchart illustrating an example of a flow of the differentiation support processing according to the first embodiment of the present invention.

FIG. 6 is a flowchart illustrating an example of a flow of the differentiation support processing. A surface layer structure differentiation classification unit 33A2 in a differentiation classification result estimation unit 33A in FIG. 3C is associated with the processing illustrated in FIG. 6.

The differentiation support unit 33 performs differentiation classification of the lesion portion based on a surface layer structure (S21).

The differentiation support unit 33 can extract the surface layer structure by a band pass filter, a Hessian matrix, a gabor filter, or the like configured to extract a specific frequency band. The differentiation support unit 33 calculates a texture feature value of the extracted surface layer structure, and classifies the texture feature value into classes by machine learning. As the texture feature value, a known technique such as an SIFT feature value, an LBP (local binary pattern) feature value, or a CoHOG (co-occurrence histograms of gradients) feature value is used. The machine learning performs classification using a powerful classifier such as an SVM (support vector machine). For a large intestine, for example, a lesion is classified into a hyperplastic polyp, an adenoma lesion, an invasive cancer, and the like.

In other words, processing in S21 configures the differentiation classification result estimation unit configured to estimate a differentiation classification result. Particularly, the processing in S21 configures the surface layer structure differentiation classification unit 33A2 configured to perform differentiation classification based on the surface layer structure of the lesion region specified by the lesion region specifying unit 33A1.

The control unit 22a displays on the monitor 13 the differentiation classification result obtained in S21 (S22).

Figure 7:
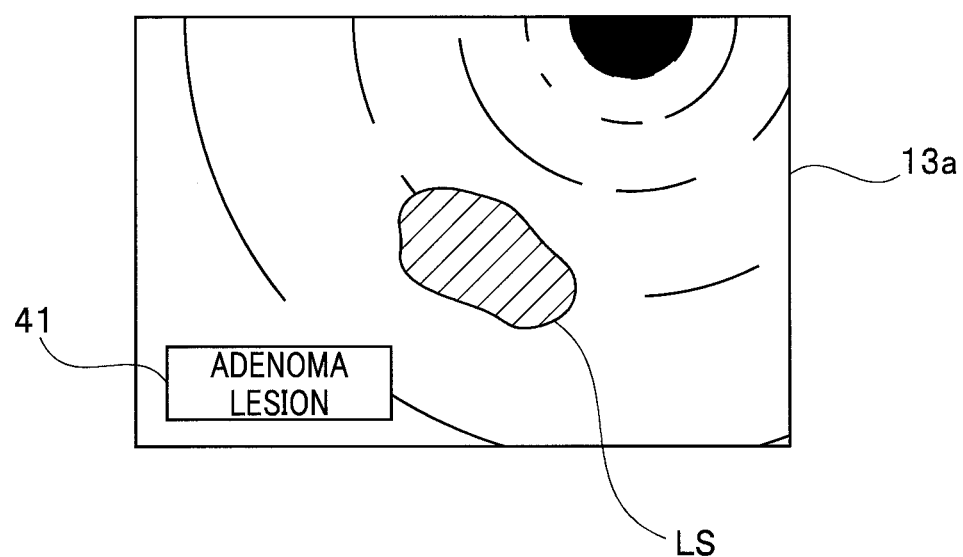
FIG. 7 is a diagram for describing an example of differentiation support information displayed on a monitor 13 according to the first embodiment of the present invention.

FIG. 7 is a diagram for describing an example of differentiation support information displayed on the monitor 13.

An endoscope image is displayed on a screen 13a of the monitor 13, and classification result information for a specified lesion region LS is displayed on a window 41 as support information. Classification result information "adenoma lesion" is displayed as the support information.

Accordingly, processing in S22 configures an information output unit configured to display the differentiation classification result estimated by the differentiation classification result estimation unit 33A as the differentiation support information on the monitor 13 as a display device.

As described above, in the endoscope apparatus according to the above-described embodiment, an image processing apparatus capable of smoothly receiving the differentiation support, when the operator differentiates the lesion portion using the endoscope, the differentiation support can be provided.

Second Embodiment

Although it is judged whether or not the distal end portion of the insertion section remains still based on the endoscope image acquired using the image pickup device to judge whether or not the operator is performing differentiation in the first embodiment, movement of a distal end portion 11a1 of an insertion section 11a is detected by a sensor, and it is judged whether or not an operator is performing differentiation based on a detection result in the present embodiment.

An endoscope apparatus according to the present embodiment has a similar configuration to the configuration of the endoscope apparatus 1 according to the first embodiment, and the same components are respectively assigned the same reference numerals, to omit description, and only different components will be described.

Figure 8:
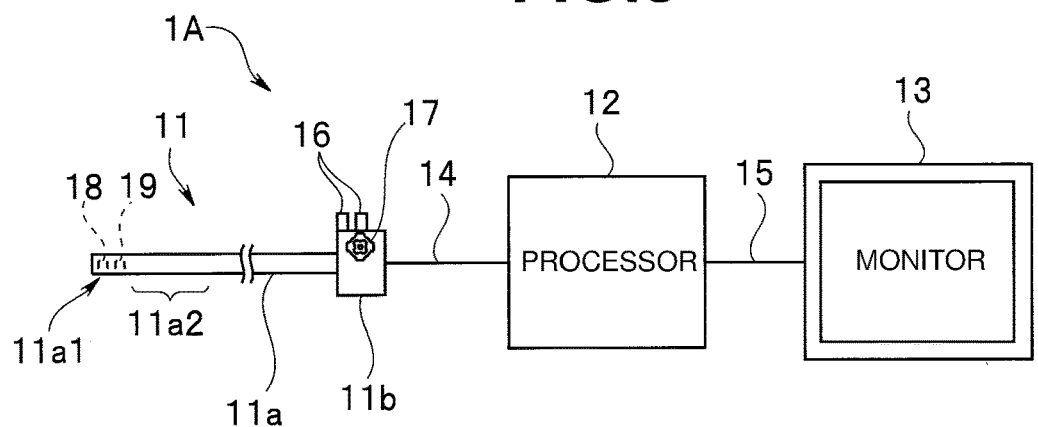
FIG. 8 is a configuration diagram of an endoscope apparatus according to a second embodiment of the present invention.
Figure 9:
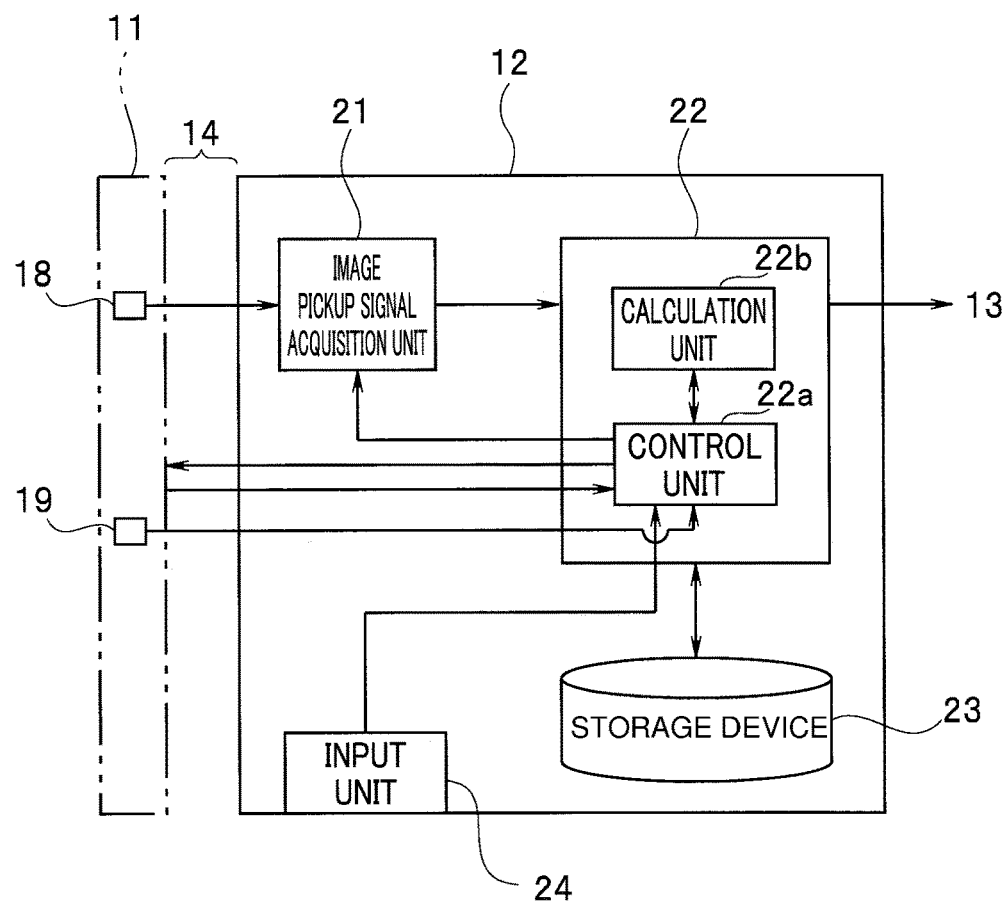
FIG. 9 is a block diagram illustrating a configuration relating to image processing of a processor 12 according to the second embodiment of the present invention.

FIG. 8 is a configuration diagram of an endoscope apparatus according to a second embodiment. FIG. 9 is a block diagram illustrating a configuration relating to image processing of a processor 12.

An acceleration sensor 19 is provided within the distal end portion 11a1 of the insertion section 11a. The acceleration sensor 19 is a triaxial acceleration sensor, for example, and detects movement in a three-dimensional direction of the distal end portion 11a1. An output signal of the acceleration sensor 19 is fed to a control unit 22a.

Since the acceleration sensor 19 outputs respective acceleration signals along three axes, the control unit 22a can detect presence or absence of the movement in the three-dimensional direction of the distal end portion 11a1 and a magnitude of an acceleration depending on a magnitude of the output signal of the acceleration sensor 19. A differentiation state judgment unit 32 in the control unit 22a judges a still state of the distal end portion 11a1 based on the output signal of the acceleration sensor 19.

Although processing illustrated in FIG. 4 to FIG. 6 is also performed in the present embodiment, the processing illustrated in FIG. 5 differs from the processing in the first embodiment.

Figure 10:
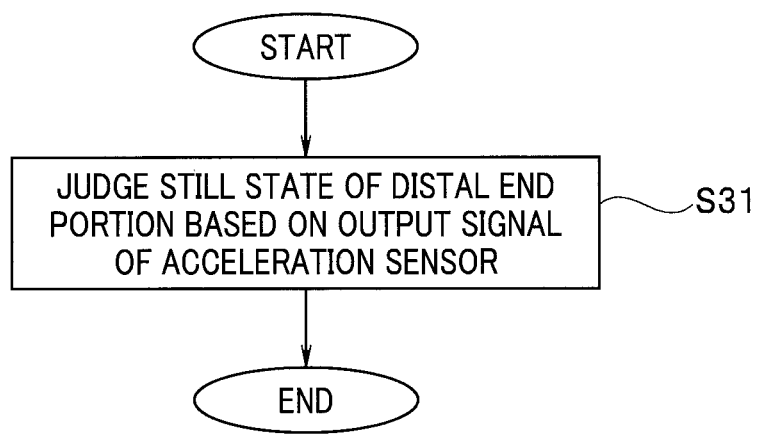
FIG. 10 is a flowchart illustrating an example of a flow of differentiation state judgment processing in the second embodiment of the present invention.

FIG. 10 is a flowchart illustrating an example of a flow of differentiation state judgment processing in the second embodiment. A distal end portion movement amount calculation unit 32A2 in a stillness judgment unit 32A in FIG. 3B is associated with the processing illustrated in FIG. 10.

The differentiation state judgment unit 32 judges the still state of the distal end portion 11a1 based on the output signal of the acceleration sensor 19 (S31).

In other words, processing illustrated in S31 configures the stillness judgment unit 32A. The stillness judgment unit 32A configures the distal end portion movement amount calculation unit 32A2 configured to calculate a movement amount of the distal end portion 11a1 based on a detection signal of the sensor configured to detect movement of the distal end portion 11a1, and judges that the distal end portion 11a1 remains still when the movement amount calculated by the distal end portion movement amount calculation unit 32A2 is less than a predetermined threshold value TH2. The movement amount also includes a rotation amount around an axis of the distal end portion 11a1.

In FIG. 4, the differentiation state judgment unit 32 judges whether the distal end portion 11a1 of the insertion section 11a remains still, i.e., a lesion portion is being differentiated based on a result of the processing in S31 illustrated in FIG. 10 (S3).

As described above, the differentiation state judgment unit 32 judges that the operator who operates the endoscope 11 is in a differentiation state where a lesion portion in an observation target of the endoscope 11 is being differentiated based on the signal from the sensor in the endoscope 11.

In the present embodiment, processing for specifying a lesion region illustrated in FIG. 4 (S4) and differentiation support processing as illustrated in FIG. 6 (S5) are also performed.

Therefore, according to the present embodiment, a similar effect to the effect in the first embodiment can also be obtained.

Third Embodiment

Although it is judged whether or not the distal end portion 11a1 of the insertion section 11a remains still based on the endoscope image acquired using the image pickup device 18 to judge whether or not the operator is performing differentiation in the first embodiment, and the movement of the distal end portion 11a1 of the insertion section 11a is detected by the sensor to judge whether or not the operator is performing differentiation based on the detection result in the second embodiment, it is judged whether or not an operator is performing differentiation based on an operation for setting an observation state in an operation section 11b in the present embodiment.

An endoscope apparatus according to the present embodiment has a similar configuration to the configuration of the endoscope apparatus 1 according to the first embodiment, and the same components are respectively assigned the same reference numerals to omit description, and only different components will be described.

Figure 11:
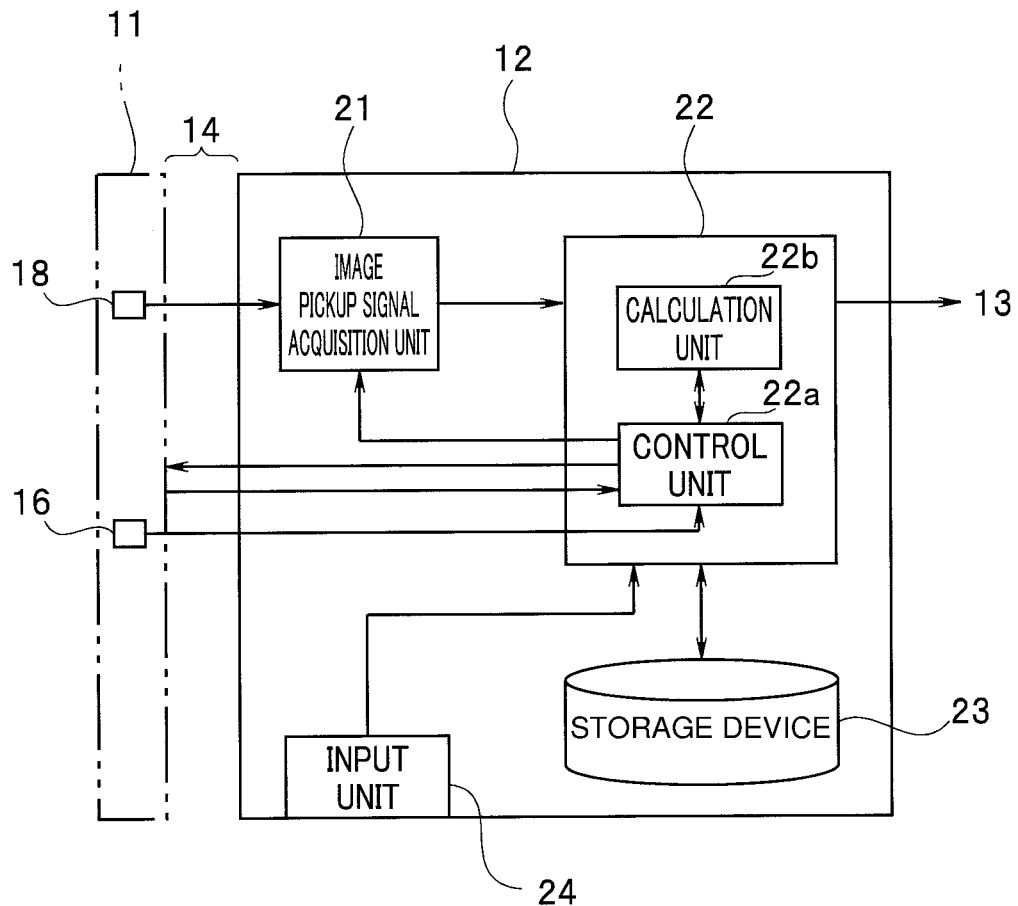
FIG. 11 is a block diagram illustrating a configuration relating to image processing of a processor 12 according to a third embodiment of the present invention.

FIG. 11 is a block diagram illustrating a configuration relating to image processing of a processor 12.

A state signal of a near point/far point observation switching button among various types of operation buttons 16 in an operation section 11b is inputted to a control unit 22a.

The operator switches the near point/far point observation switching button to a near point observation mode to closely observe a lesion portion when performing differentiation. In the near point observation mode, an image within a subject is enlarged by image processing or a zoom lens mechanism not illustrated, and is displayed on a monitor 13. In the near point observation mode, i.e., at the time of enlargement observation, it can be estimated that differentiation is being performed.

Figure 12:
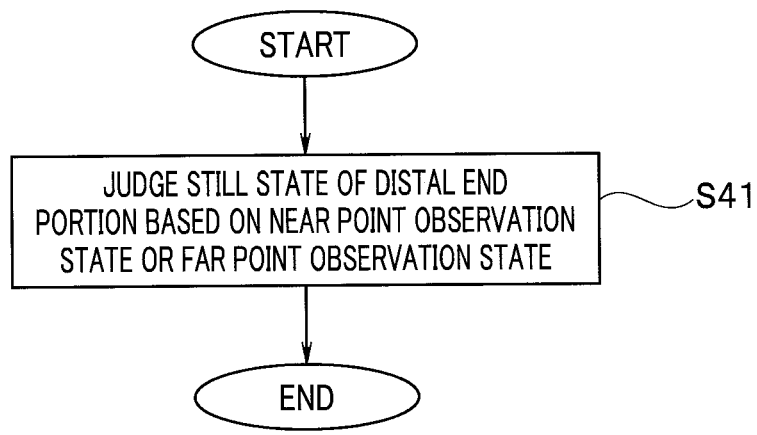
FIG. 12 is a flowchart illustrating an example of a flow of differentiation state judgment processing in the third embodiment of the present invention.

FIG. 12 is a flowchart illustrating an example of a flow of differentiation state judgment processing in the third embodiment. A differentiation operation judgment unit 32B in a differentiation state judgment unit 32 in FIG. 3B is associated with the processing illustrated in FIG. 12.

The differentiation state judgment unit 32 judges that the operator who operates an endoscope 11 is in a differentiation state where a lesion portion in an observation target of the endoscope 11 is being differentiated based on an operation signal to the endoscope 11. The differentiation state judgment unit 32 judges a still state of a distal end portion 11a1 based on an operation state signal of the near point/far point observation switching button (S41). When the near point/far point observation switching button is set to a near point observation state, it is judged that the operator is performing differentiation. Processing in S41 configures the differentiation operation judgment unit 32B configured to judge that the operator is in the differentiation state based on an observation state of the endoscope 11.

In FIG. 4, the differentiation state judgment unit 32 judges whether or not the lesion portion is being differentiated based on a result of the processing in S41 illustrated in FIG. 12, i.e., based on a setting operation signal for near point observation or enlargement observation to the endoscope 11 (S3).

In the present embodiment, processing for specifying a lesion region illustrated in FIG. 4 (S4) and differentiation support processing as illustrated in FIG. 6 (S5) are also performed.

Therefore, according to the present embodiment, a similar effect to the effect in the first embodiment can be obtained.

Then, modifications to the above-described three embodiments will be described.

Although each of the following modifications is implemented in an endoscope apparatus including the same components as the components in the endoscope apparatus according to each of the above-described embodiments, the same components as the components in the endoscope apparatus according to each of the embodiments are respectively assigned the same reference numerals in each of the modifications, and only components associated with the modification will be described.

(Modification 1)

Although it is judged whether or not the distal end portion 11a1 of the insertion section 11a remains still based on the movement amount of the entire image, and it is judged that the operator is performing differentiation when the movement amount is the predetermined threshold value TH1 or less in the first embodiment, it is judged that an operator is performing differentiation based on whether or not the operator is gazing at a certain region even if a distal end portion 11a1 of an insertion section 11a moves in the present modification.

Although a differentiation state judgment unit 32 in a processor 12 in the present modification performs processing from FIG. 4 to FIG. 6, differentiation state judgment processing in S2 illustrated in FIG. 4 (the processing illustrated in FIG. 5) differs from the processing in the first embodiment.

Figure 13:
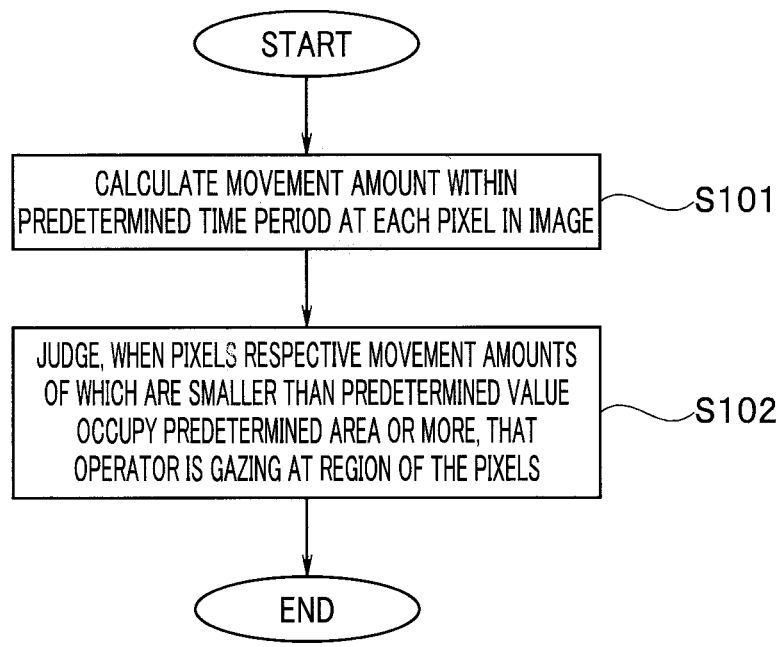
FIG. 13 is a flowchart illustrating an example of a flow of differentiation state judgment processing in a modification 1.

FIG. 13 is a flowchart illustrating an example of a flow of the differentiation state judgment processing in the present modification. A pixel movement amount calculation unit 32C1 in a gaze judgment unit 32C in FIG. 3B is associated with the processing illustrated in FIG. 13.

The differentiation state judgment unit 32 calculates a movement amount within a predetermined time period at each of pixels in an image based on two images having intervals of a predetermined time period T therebetween (S101).

More specifically, a movement amount for each of the pixels is calculated using a method for searching, for each of small regions in the image, for a part appropriate as the small region at a movement destination, for example, a known Lucas-Kanade method.

The Lucas-Kanade method is described in "Digital Image Processing" (revised new edition) published by Computer Graphic Arts Society (CG-ARTS), pp. 291.

The differentiation state judgment unit 32 judges that the operator is gazing at a region of the pixels (S102), when the pixels the respective movement amounts of which are smaller than a predetermined value occupy a predetermined area or more.

In other words, the differentiation state judgment unit 32 includes the gaze judgment unit 32C configured to judge whether or not the operator is gazing at the same region of the observation target, and judges that the operator is in a differentiation state when the gaze judgment unit 32C judges that the operator is gazing at the same region. The gaze judgment unit 32C includes the pixel movement amount calculation unit 32C1 configured to calculate a movement amount for each of pixels in an endoscope image, and judges that the operator is gazing at the same region when the pixels the respective movement amounts of which are small occupy a predetermined area.

The operator may not only make the distal end portion 11a1 still to observe a certain site but also observe the site in various directions to differentiate a lesion portion.

Therefore, according to the present modification, the operator moves the distal end portion 11a1 to change a direction of a line of sight, to judge whether or not a certain region is being observed in various directions depending on whether or not the region of the pixels the respective movement amounts within a predetermined time period of which are smaller than a predetermined value has a predetermined area or more.

When it is judged in S102 that the operator is gazing, it is judged in S3 illustrated in FIG. 4 that the operator is performing differentiation.

Therefore, according to the present modification, it can be judged that the operator is performing differentiation even when the distal end portion 11a1 does not remain still.

Therefore, the gaze judgment in the present modification is also performed in addition to the judgment whether or not the distal end portion 11a1 remains still in the first and second embodiments, so that it can be judged with higher accuracy whether or not the operator is performing differentiation.

(Modification 2)

Although it is judged whether or not the distal end portion 11a1 of the insertion section 11a remains still based on the movement amount of the entire image to judge that the operator is performing differentiation when the movement amount is the predetermined threshold value TH1 or less in the first embodiment. It is judged that the operator is performing differentiation based on whether or not the operator is gazing at a certain region even if the distal end portion 11a1 of the insertion section 11a moves in the above-described modification 1. It is judged from an image which of enlargement observation and proximity observation is being performed to observe a site within a subject to judge that an operator is performing differentiation based on a judgment result in a modification 2.

Although a differentiation state judgment unit 32 in a processor 12 in the present modification performs processing from FIG. 4 to FIG. 6, differentiation state judgment processing in S2 illustrated in FIG. 4 (the processing illustrated in FIG. 5) differs from the processing in the first embodiment.

Figure 14:
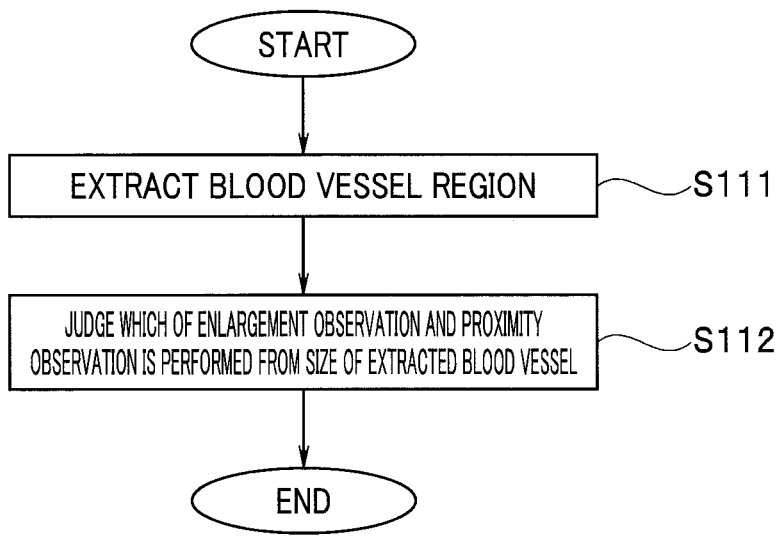
FIG. 14 is a flowchart illustrating an example of a flow of differentiation state judgment processing in a modification 2.

FIG. 14 is a flowchart illustrating an example of a flow of the differentiation state judgment processing in the present modification. A blood vessel region extraction unit 32D in FIG. 3B is associated with the processing illustrated in FIG. 14.

A differentiation state judgment unit 32 extracts a blood vessel region in an image obtained in a predetermined cycle (S111).

More specifically, a region where respective luminance values of pixels are concave, i.e., the luminance values are low is extracted as the blood vessel region using a known gabor filter or Hessian matrix, for example.

A region of a capillary blood vessel a mucosal surface of which has been emphasized is extracted in a narrow band light observation mode using narrow band light having a center wavelength of 415 nm and narrow band light having a center wavelength of 540 nm, and a region of a blood vessel in an image is extracted in a normal light observation mode.

The differentiation state judgment unit 32 judges which of enlargement observation and proximity observation is performed from a size of a blood vessel in the blood vessel region extracted in S111 (S112).

More specifically, when the extracted blood vessel region is subjected to two-dimensional Fourier transform to acquire frequency components, and if the acquired frequency components are unevenly distributed toward lower frequencies than a predetermined threshold value, the differentiation state judgment unit 32 judges that enlargement or proximity observation is being performed. In other words, the differentiation state judgment unit 32 includes the blood vessel region extraction unit 32D configured to extract a blood vessel region from an endoscope image, and judges that the operator is in a differentiation state based on the size of the blood vessel extracted by the blood vessel region extraction unit 32D.

When it is judged that the enlargement observation is being performed, differentiation classification corresponding to the enlargement observation can also be performed in a differentiation support unit 33. For example, for a large intestine, differentiation classification can be performed using an SVM configured to learn image data collected based on Hiroshima classification, which is a lesion classification, as teacher data, for example.

Accordingly, a similar effect to the effect in each of the above-described embodiments can be obtained according to the present modification.

(Modification 3)

Although the differentiation classification of the lesion portion is being performed based on the surface layer structure in the differentiation support processing in each of the above-described embodiments and modifications, differentiation classification of a lesion portion may be performed based on shape information of the lesion portion.

In the present modification, the differentiation classification of the lesion portion is performed based on the shape information of the lesion portion, and a differentiation result is displayed on a monitor.

Figure 15:
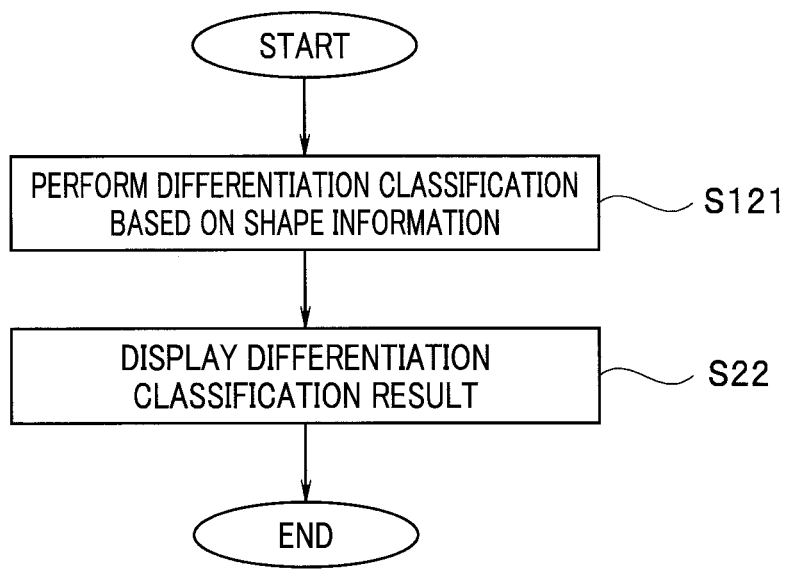
FIG. 15 is a flowchart illustrating an example of a flow of differentiation support processing in a modification 3.

FIG. 15 is a flowchart illustrating an example of a flow of differentiation support processing in the present modification. A shape differentiation classification unit 33A3 in FIG. 3C is associated with the processing illustrated in FIG. 15.

A differentiation support unit 33 performs differentiation classification of a lesion portion based on shape information (S121). Processing in S121 configures the shape differentiation classification unit. In other words, the differentiation support unit 33 includes the shape differentiation classification unit 33A3 configured to perform the differentiation classification based on a shape of the lesion portion.

More specifically, the differentiation support unit 33 generates a mask image representing a lesion region, and calculates a shape feature value based on the image. The shape feature value is classified into one of a plurality of classes generated by machine learning using a classifier such as an SVM. As a shape feature value, known parameters such as a roundness, a moment, and a fractal dimension are used.

Examples of a colon polyp include a protruded type (I type) colon polyp and a surficial type (II type) colon polyp, and examples of the protruded type colon polyp include a sessile (Is) colon polyp having no constriction in its rising portion, a semipedunculated (Isp) colon polyp having a constriction in its rising portion, and a pedunculated (Ip) colon polyp having a stalk. The surficial type colon polyp is classified into an elevated type (IIa) colon polyp, a flat type (IIb) colon polyp, a depressed type (IIc) colon polyp, and the like.

A control unit 22a displays a differentiation classification result obtained in S121 on a monitor (S22).

Therefore, according to the present modification, a similar effect to the effect in each of the above-described embodiments can be obtained while the shape information of the lesion portion is presented as support information to an operator. Thus, the operator can obtain more detailed information about the lesion portion.

Note that the differentiation classification of the lesion portion may be performed simultaneously for a surface layer structure of the lesion portion and the shape information of the lesion portion.

(Modification 4)

Although the differentiation classification of the lesion portion is performed based on the surface layer structure in the differentiation support processing in each of the above-described embodiments and modifications, differentiation classification of a lesion portion may be performed based on a size of the lesion portion.

In the present modification, differentiation classification of a lesion portion is performed based on size information of the lesion portion, and a differentiation result is displayed on a monitor.

Figure 16:
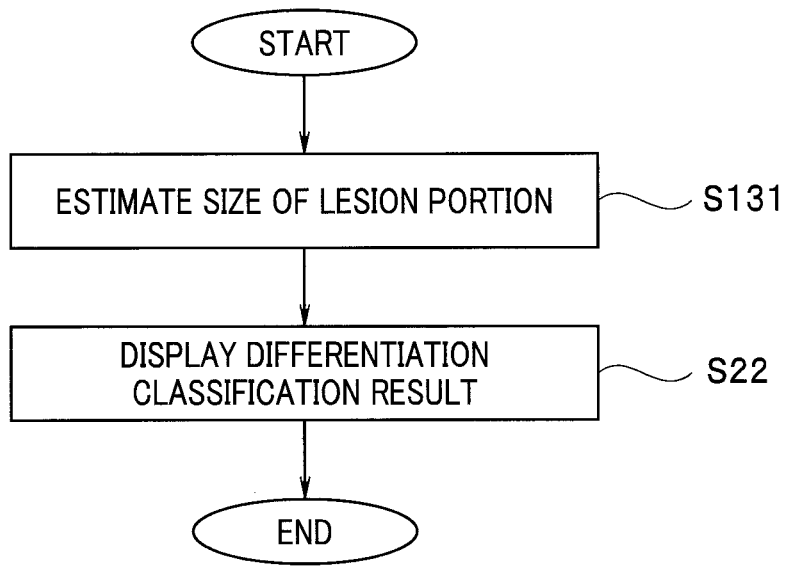
FIG. 16 is a flowchart illustrating an example of a flow of differentiation support processing in a modification 4.

FIG. 16 is a flowchart illustrating an example of a flow of differentiation support processing in the present modification. A size estimation unit 33A4 in FIG. 3C is associated with the processing illustrated in FIG. 16.

A differentiation support unit 33 estimates a size of a lesion portion (S131). Processing in S131 configures the size estimation unit 33A4 configured to estimate the size of the lesion portion. In other words, the differentiation support unit 33 includes the size estimation unit 33A4 configured to estimate the size of the lesion portion.

Figure 17:
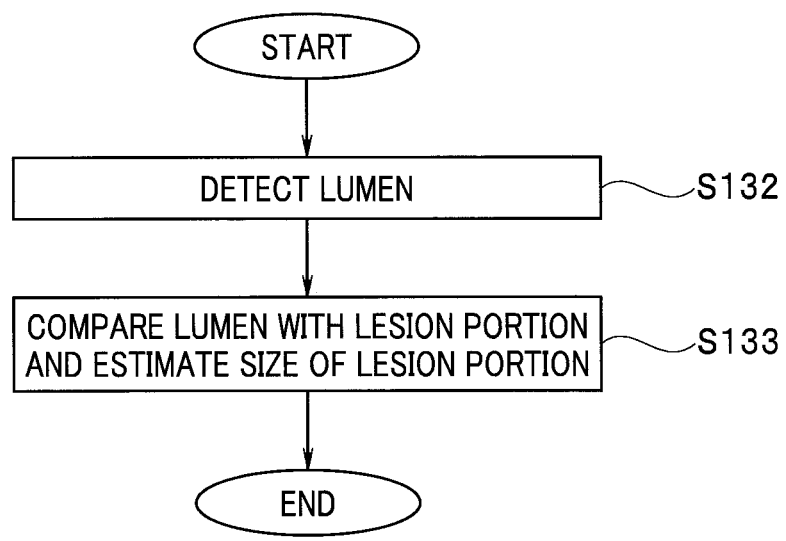
FIG. 17 is a flowchart illustrating an example of a flow of lesion size estimation processing in the modification 4.

More specifically, the differentiation support unit 33 estimates the size of the lesion portion by lesion size estimation processing illustrated in FIG. 17.

FIG. 17 is a flowchart illustrating an example of a flow of the lesion size estimation processing.

The differentiation support unit 33 detects a lumen (S132).

In S132, an image pickup distance to each of pixels in an image is estimated. Estimation of a shooting distance assuming a shooting target as a lambertian surface based on the image among various known techniques will be described.

More specifically, a low absorption wavelength (e.g., red (R) wavelength) component in which a degree of absorption or scattering within a living body is lowest is first selected as a low absorption wavelength component. This is to inhibit a pixel value from decreasing by a blood vessel or the like reflected on a mucosal surface and to obtain pixel value information most strongly correlated with an image pickup distance from the mucosal surface. In an image including three components in red (R), green (G), and blue (B), the red (R) component is selected because the red (R) component is a component having a wavelength separated from an absorption band of blood and having a long wavelength and is not easily affected by the absorption or scattering within the living body.

The differentiation support unit 33 estimates an image pickup distance assuming the lambertian surface based on a pixel value of the low absorption wavelength component. More specifically, the image pickup distance is calculated by the following equation (2).

[Expression 2]

$$r = \sqrt{\frac{I \times K \times \cos\theta}{L}} \quad (2)$$

Here, r indicates an image pickup distance, I indicates a radiation intensity of a light source obtained by previous measurement, and K indicates a diffuse reflection coefficient on a mucosal surface as an average value previously measured. θ indicates an angle formed between a normal vector on the mucosal surface and a vector from the surface to the light source, and is a value determined by a positional relationship between the light source in the distal end portion 11*a*1 of the insertion section 11*a* and the mucosal surface, and an average value is previously set. L indicates an R component value of a pixel, on which the mucosal surface is reflected, as an image pickup distance estimation target.

Note that correction of pixel value unevenness by an optical system or an illumination system which can cause a decrease in accuracy of each processing, mirror reflection, and elimination of a non-mucosal region such as a residue or a bubble may be performed before the image pickup distance is estimated.

Although a method based on the image is illustrated here, the image pickup distance may be calculated based on a distance measurement sensor in addition to the method. The image pickup distance need not necessarily be estimated, but adaptive processing in succeeding stages may be performed using a pixel value correlated with the image pickup distance.

Then, the differentiation support unit 33 provides, for an image pickup distance of a pixel in the vicinity of a lesion, a threshold value smaller and a threshold value larger than the image pickup distance, and extracts a region of an image pickup distance band where there is a lesion by processing of the threshold values. The differentiation support unit 33 calculates a roundness of the region, and detects, when the roundness is more than a predetermined value, the region as a lumen.

The differentiation support unit 33 compares the lumen with the lesion portion, and estimates the size of the lesion portion (S133) after S131.

More specifically, the differentiation support unit 33 calculates a ratio of a length of a lesion to a circumferential length of the detected lumen, to estimate an actual size of the legion. Note that an accuracy of size estimation can also be improved by previously setting a circumferential length of a lumen in each of organ sites (positions) based on anatomy. When a large intestine is inspected, for example, an accuracy of size estimation may be improved by estimating a site (position) of a lesion portion of the large intestine from an insertion amount of the insertion section 11*a* and comparing a circumferential length of a lumen in the site with a circumferential length of the lumen previously set.

As described above, the size estimation unit 33A4 estimates the size of the lesion portion by comparing the size of the lesion portion with a circular size of the lumen captured in the endoscope image.

A control unit 22*a* displays information about the size of the lesion portion obtained in S133 as a differentiation classification result on a monitor 13 (S22).

Therefore, according to the present modification, a similar effect to the effect in each of the above-described embodiments can be obtained while the size information of the lesion portion is presented as support information to an operator. Thus, the operator can obtain more detailed information about the lesion portion.

Note that the differentiation classification of the lesion portion may be performed by simultaneously estimating a surface layer structure of the lesion portion and a size of the lesion portion, simultaneously estimating shape information of the lesion portion and the size of the lesion portion, or simultaneously estimating a surface layer structure of the lesion portion, shape information of the lesion portion, and the size of the lesion portion.

(Modification 5)

Although the differentiation classification of the lesion portion is not associated with set observation light in the differentiation support processing in each of the above-described embodiments and modifications, differentiation classification of a lesion portion may be performed depending on observation light.

In the present modification, differentiation classification of a lesion portion is performed depending on observation light, and a differentiation result is displayed on a monitor.

Figure 18:
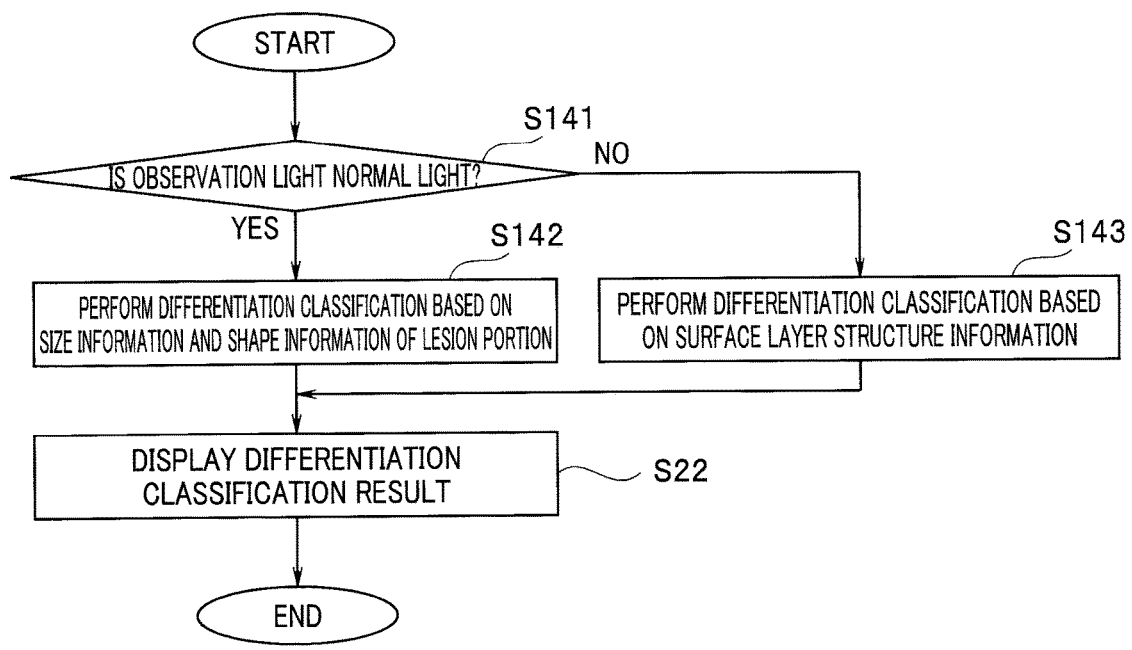
FIG. 18 is a flowchart illustrating an example of a flow of differentiation support processing in a modification 5.

FIG. 18 is a flowchart illustrating an example of a flow of differentiation support processing in the modification 5. A differentiation operation classification unit 33A5*a* and an observation light judgment unit 33A5*a*1 in a differentiation operation judgment unit 33A5 and a differentiation index switching unit 33A6 in FIG. 3C are associated with the processing illustrated in FIG. 18.

In FIG. 18, when an endoscope apparatus has two observation modes, i.e., a normal light observation mode and a narrow band light observation mode, support information, e.g., differentiation indexes respectively outputted in the observation modes differ from each other. Normal light is light for obtaining an endoscope image when an object is irradiated with white light, and narrow band light as special light is light for obtaining an endoscope image when the object is irradiated with predetermined narrow band light.

A differentiation support unit 33 judges whether or not observation light currently emitted is normal light (S141). In other words, it is judged which of the normal light observation mode and the narrow band light observation mode is the observation mode. Accordingly, it can be judged whether or not the observation light is the normal light based on information about the set observation mode or control of a light source.

When the observation light is normal light (S141: YES), the differentiation support unit 33 performs differentiation classification based on size information and shape information of the lesion portion (S142).

When the observation light is not normal light (S141: NO), the differentiation support unit 33 performs differentiation classification based on surface layer structure information (S143).

After S142 and S143, the differentiation support unit 33 displays on a monitor 13 a differentiation classification result based on the size information and the shape information of the lesion portion or a differentiation classification result based on the surface layer structure information as a differentiation classification result (S22).

As described above, the differentiation operation judgment unit 33A5 includes the differentiation operation classification unit 33A5a configured to classify a differentiation operation by an operator, and the differentiation operation classification unit 33A5a includes the observation light judgment unit 33A5a1 configured to judge which of the normal light and the special light is the observation light. A differentiation classification result estimation unit 33A includes the differentiation index switching unit 33A6 configured to switch a differentiation index based on the differentiation operation classified by the differentiation operation classification unit 33A5a, and the differentiation index switching unit 33A6 switches the differentiation index based on the observation light judged by the observation light judgment unit 33A5a1.

Therefore, according to the present modification, a similar effect to the effect in each of the above-described embodiments can be obtained while the operator can obtain the support information corresponding to the observation light.

Note that although it is judged from the image which of the enlargement observation and the proximity observation is being performed in the above-described modification 2, a differentiation operation classification unit 33A5a may also include an enlargement/proximity judgment unit 33A5a2 configured to judge which of an enlargement observation operation and a proximity observation operation is performed, to classify a differentiation operation, and a differentiation classification result estimation unit 33A may switch a differentiation index based on the differentiation operation classified by the differentiation operation classification unit 33A5a in the modification 2.

(Modification 6)

Although the classification result information such as "adenoma lesion" is outputted as support information in the differentiation support processing in each of the above-described embodiments and modifications, site information of an organ may be outputted.

Figure 19:
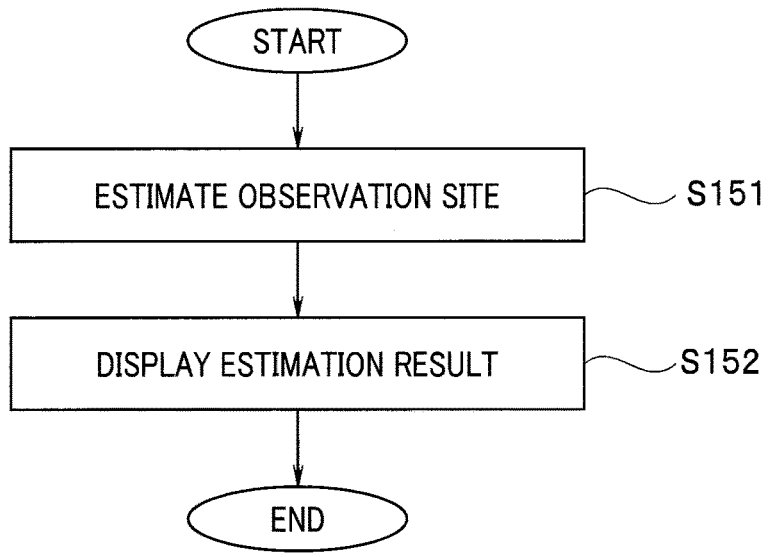
FIG. 19 is a flowchart illustrating an example of a flow of differentiation support processing in a modification 6.

FIG. 19 is a flowchart illustrating an example of a flow of differentiation support processing in the present modification. An organ site estimation unit 33B in FIG. 3C is associated with the processing illustrated in FIG. 19.

A differentiation support unit 33 estimates an observation site (S151). For example, a rectum, a sigmoid colon, a descending colon, a transverse colon, an ascending colon, and a cecum are recognized when an organ to be observed is a large intestine. A cardia, a fundus ventriculi, a corpus ventriculi, an angulus ventriculi, an antrum, a pylorus, and a duodenum are recognized when the organ to be observed is a stomach. A jejunum and an ileum are recognized when the organ is a small intestine. A cervical esophagus, a thoracic esophagus, and an abdominal esophagus are recognized when the organ is an esophagus. More specifically, when image data in which the organs are respectively captured are collected, and machine learning is performed using the image data, a site (position) can be estimated using an SVM or the like.

The differentiation support unit 33 displays an estimation result on the monitor 13 (S152). For example, characters representing an estimation result, e.g., a site being observed such as "cardia" are displayed as support information on a window 41 illustrated in FIG. 7.

As described above, the differentiation support unit 33 includes an organ site estimation unit 33B configured to estimate a site (position) of an organ as an observation target of an endoscope 11. The organ site estimation unit 33B estimates a rectum, a sigmoid colon, a descending colon, a transverse colon, an ascending colon, or a cecum when the organ is a large intestine, estimates a cardia, a fundus ventriculi, a corpus ventriculi, an angulus ventriculi, an antrum, a pylorus, or a duodenum when the organ is a stomach, estimates a jejunum or an ileum when the organ is a small intestine, and estimates a cervical esophagus, a thoracic esophagus, or an abdominal esophagus when the organ is an esophagus.

According to the present modification, a similar effect to the effect in each of the above-described embodiments can be obtained while an operator can obtain information about an observation site as support information.

(Modification 7)

Although the support information is outputted as a message onto the monitor 13 in the differentiation support in each of the above-described embodiments and modifications, a clear image is selected from among a plurality of obtained images and is displayed on a monitor 13 in the present modification.

Figure 20:
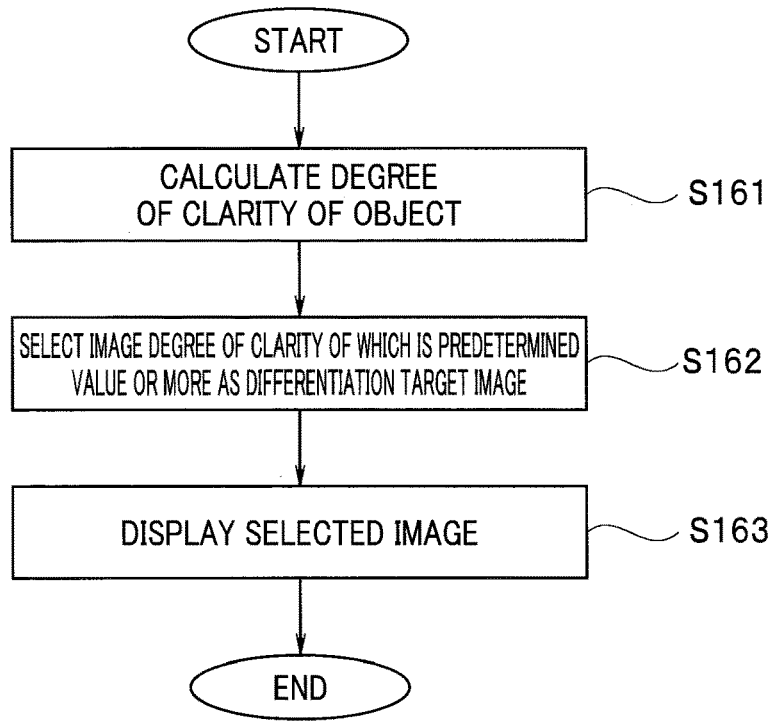
FIG. 20 is a flowchart illustrating an example of a flow of differentiation support processing in a modification 7.

FIG. 20 is a flowchart illustrating an example of a flow of differentiation support processing in the present modification. A clarity calculation unit 33C1 in a differentiation target image selection unit 33C in FIG. 3C is associated with the processing illustrated in FIG. 20.

A differentiation support unit 33 calculates a degree of clarity of an object (S161).

More specifically, a degree of clarity is calculated for a lesion region in an image specified by a lesion region specifying unit 33A1. The degree of clarity is acquired by calculating any one of or a combination of any two or more of a color shift amount, a degree of blur, a noise amount, a luminance saturation area ratio, contrast information, frequency information, and edge information, or by calculating a plurality of degrees of clarity. Such values can be calculated as follows as a known technique. The color shift amount is acquired by calculating an average saturation value. The degree of blur is acquired by calculating an average value of a range of a specific frequency component. The noise amount is acquired by calculating the number of pixels deviating from a standard deviation by a predetermined value or more. The luminance saturation area ratio is acquired by calculating a region an R color component of which is a predetermined value or more divided by an area of a lesion region. The edge information is acquired by calculating an amount of an edge judgment pixel value having a predetermined intensity.

The differentiation support unit 33 selects as a differentiation target image an image a degree of clarity in a lesion portion of which is a predetermined value or more (S162). The differentiation support unit 33 can generate and output support information based on the selected image.

As described above, the differentiation support unit 33 includes a differentiation target image selection unit 33C configured to select a target image significant for differentiation. The differentiation target image selection unit 33C includes a clarity calculation unit 33C1 configured to calculate the degree of clarity of the lesion region specified by the lesion region specifying unit 33A1. The degree of clarity calculated by the clarity calculation unit 33C1 is one or more of a color shift amount, a degree of blur, a noise amount, a luminance saturation area ratio, or edge information.

The differentiation support unit 33 displays the image selected in S162 on the monitor 13 (S163).

Therefore, according to the present modification, a similar effect to the effect in each of the above-described embodiments can be obtained while an operator can see an endoscope image including a clear lesion portion.

(Modification 8)

Although the support information is outputted as a message onto the monitor 13 in the differentiation support in each of the above-described embodiments and modifications, an image in which a predetermined important region is captured is selected and displayed on a monitor 13.

Figure 21:
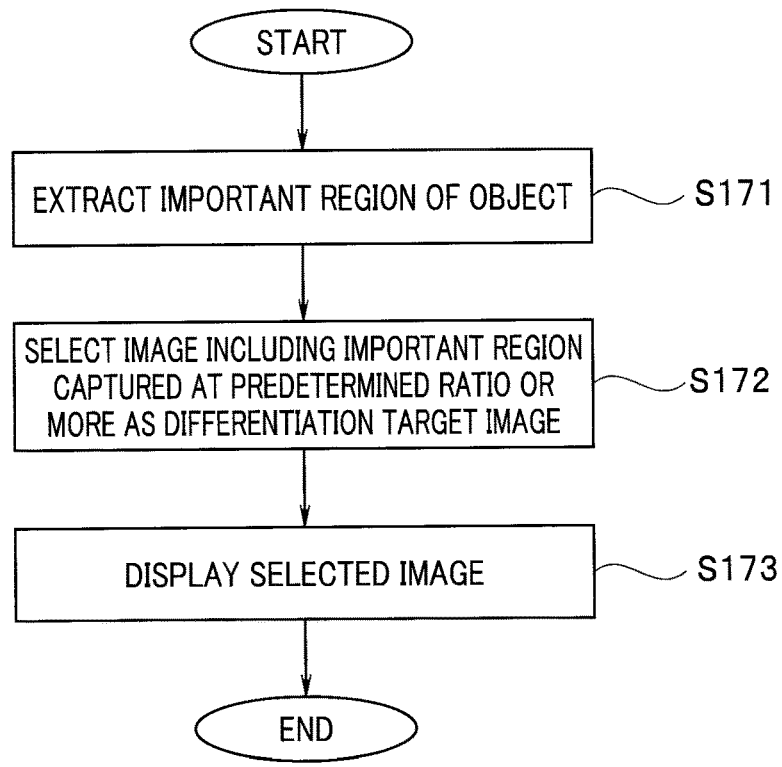
FIG. 21 is a flowchart illustrating an example of a flow of differentiation support processing in a modification 8.

FIG. 21 is a flowchart illustrating an example of a flow of differentiation support processing in the present modification. A predetermined region calculation unit 33C2 in a differentiation target image selection unit 33C in FIG. 3C is associated with the processing illustrated in FIG. 21.

A differentiation support unit 33 extracts an important region of an object (S171). The important region is classified into one of a plurality of classes generated by machine learning using a classifier such as an SVM based on a predetermined shape feature value. The important region is a predetermined region such as a raised top portion or a raised rising portion for a large intestine polyp, for example. For example, when image data in which the important region is captured are collected and a tendency of the image data is learned using the image data as teacher data, the important region can be extracted.

The differentiation support unit 33 selects an image including the important region captured at a predetermined ratio or more as a differentiation target image (S172). The differentiation support unit 33 can generate and output support information based on the selected image.

As described above, the differentiation target image selection unit 33C includes the predetermined region ratio calculation unit 33C2 configured to calculate a ratio of the predetermined region. The predetermined region for the large intestine polyp is a raised top portion or a raised rising portion of a lesion portion.

The differentiation support unit 33 displays the image selected in S172 on the monitor 13 (S173).

Therefore, according to the present modification, a similar effect to the effect in each of the above-described embodiments can be obtained while an operator can see an endoscope image including the important region, for the large intestine polyp, which is the raised top portion.

(Modification 9)

Although the differentiation support unit 33 displays the support information on the monitor 13 when the distal end portion 11a1 remains still in each of the above-described embodiments and modifications, a display amount of support information may be changed depending on a still state, i.e., depending on whether a distal end portion 11a1 remains completely still, slightly moves, or significantly moves.

Figure 22:
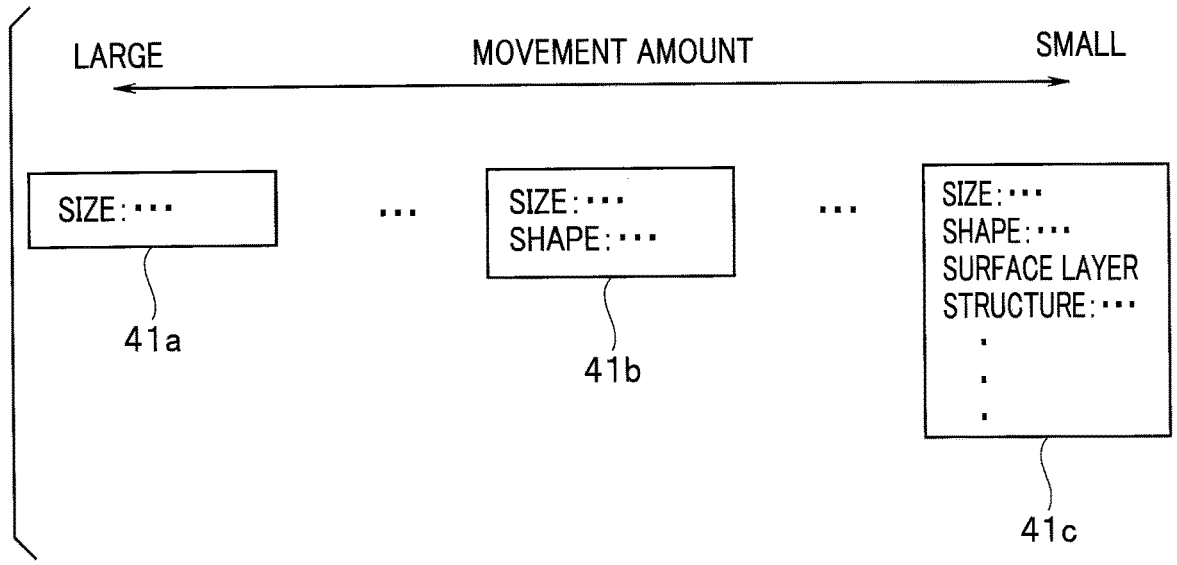
FIG. 22 is a diagram for describing how a display state of support information changes depending on a movement amount of a distal end portion of an insertion section in a modification 9.

FIG. 22 is a diagram for describing how a display state of support information changes depending on a movement amount of the distal end portion 11a1 of an insertion section 11a in the present modification.

A stillness judgment unit 32A judges a still state of the distal end portion 11a1 using an image or a sensor. The movement amount of the distal end portion 11a1 changes from a small amount to a large amount when the distal end portion 11a1 remains almost completely still or only slightly moves, for example.

A movement amount calculation unit 32A1 or a distal end portion movement amount calculation unit 32A2 each calculates the movement amount of the distal end portion 11a1. A range in which the calculated movement amount is from a small amount to a large amount is divided into a plurality of levels, and an amount of support information displayed on a differentiation support unit 33 is changed depending on each of the levels.

Even when the movement amount is large, the support information to be calculated becomes less as illustrated on a window 41a in FIG. 22 if support information can be calculated. However, the less support information is displayed on the window 41a.

If the movement amount is small, support information which can be calculated is displayed on a window 41c. If the movement amount falls into the middle degree, support information is displayed on a window 41b in a range in which the support information can be calculated. This is because there is a differentiation classification result which can be estimated even when the movement amount falls into a certain range, there is another differentiation classification result which can be estimated if the movement amount is small, and there is further a differentiation classification result which cannot be estimated unless the movement amount is zero or approximately zero. As a result, the support information is adaptively switched depending on the movement amount of the distal end portion 11a1 or depending on a degree of a still state of the distal end portion 11a1.

In other words, the movement amount calculation unit 32A1 or the distal end portion movement amount calculation unit 32A2 in a differentiation state judgment unit 32 each calculates the movement amount of the distal end portion 11a1 of the insertion section 11a in the endoscope 11 and judges a movement level of the calculated movement amount. It is judged which of a plurality of levels the movement amount has. A differentiation classification result estimation unit 33A in a differentiation support unit 33 changes an amount of support information to be outputted depending on the judgment level judged in the differentiation state judgment unit 32. The support information to be displayed on a monitor 13 changes depending on the level.

As described above, according to the present modification, a similar effect to the effect in each of the above-described embodiments can be obtained while an operator can acquire the support information which can be calculated depending on the still state.

(Modification 10)

Although the support information is outputted as a message onto the monitor 13 in the differentiation support in each of the above-described embodiments and modifications, an endoscope image, which has been subjected to image emphasis processing for facilitating observation is displayed on a monitor 13.

Figure 23:
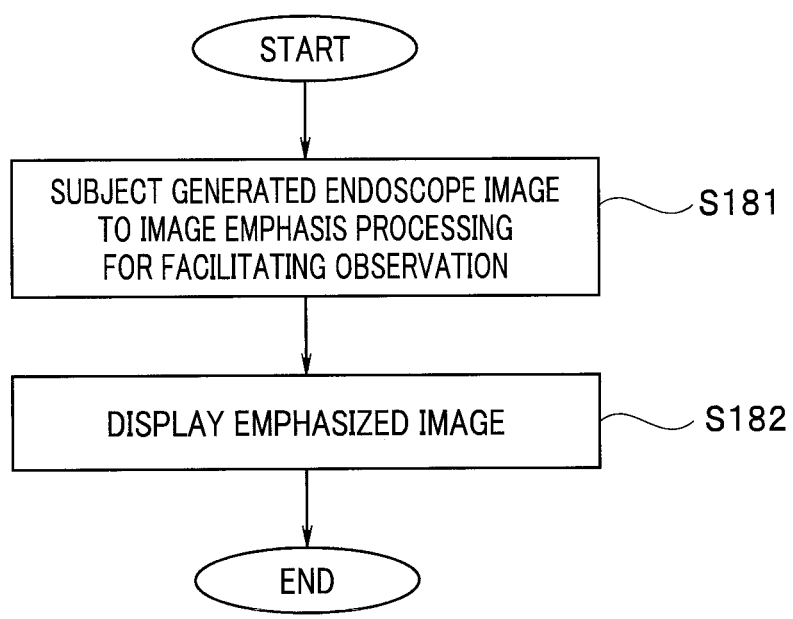
FIG. 23 is a flowchart illustrating an example of a flow of differentiation support processing in a modification 10.

FIG. 23 is a flowchart illustrating an example of a flow of differentiation support processing in the present modification. An image emphasis unit 33D in FIG. 3C is associated with the processing illustrated in FIG. 23.

A differentiation support unit 33 subjects a generated endoscope image to image emphasis processing for facilitating observation (S181).

In other words, the differentiation support unit 33 includes an image emphasis unit 33D configured to subject an endoscope image obtained by an endoscope 11 to predetermined emphasis processing, i.e., emphasis processing for an operator to differentiate a lesion portion more easily when a differentiation state judgment unit 32 judges that the operator is in a differentiation state where an observation target of the endoscope 11 is being differentiated.

Therefore, according to the present modification, a similar effect to the effect in each of the above-described embodiments can be obtained while the operator can see an endoscope image which has been subjected to image emphasis for the operator to differentiate a lesion portion more easily.

As described above, according to each of the above-described embodiments and modifications, there can be provided an image processing apparatus in which the operator can smoothly receive, when differentiating the lesion portion using the endoscope, support of the differentiation.

The present invention is not limited to only the above-described embodiments, but can be subjected to various changes and alterations, for example, without departing from the scope and spirit of the present invention.

What is claimed is:

1. An image processing apparatus comprising:
a processor comprising hardware, wherein the processor is configured to:
  receive a plurality of images of a tissue including a lesion portion, the plurality of images being received from an endoscope operated by an operator;
  judge, based on a signal from the endoscope, whether or not to engage a differentiation classification operation to classify the lesion portion in one or more of the plurality of images;
  in response to judging that the differentiation classification operation is engaged,
    process the plurality of images to specify the lesion portion within the one or more of the plurality of images; and
    perform differentiation classification on the one or more images in which the lesion portion is specified to classify the lesion portion into at least one class of a plurality of classes; and
  in response to judging that the differentiation classification operation is not engaged, not process the plurality of images to specify the lesion portion within the one or more of the plurality of images, and
wherein the processor is configured to:
  judge, based on the signal from the endoscope, whether or not a distal end of an insertion section of the endoscope is still;
  in response to judging that the distal end of the insertion section is still, judge that the differential classification operation is engaged; and
  in response to judging that the distal end of the insertion section is not still, judge that the differential classification operation is not engaged.

2. The image processing apparatus according to claim 1, wherein the processor is configured to:
  calculate a movement amount in a predetermined time period within the plurality of images;
  judge whether the movement amount in the predetermined time period within the plurality of images is less than a predetermined threshold value;
  in response to judging that the movement amount in the predetermined time period within the plurality of images is less than the predetermined threshold value, judge that the movement amount of the distal end of the insertion section is still; and
  in response to judging that the movement amount in the predetermined time period within the plurality of images is not less than the predetermined threshold value, judge that the movement amount of the distal end of the insertion section is not still.

3. The image processing apparatus according to claim 1, wherein the processor is configured to:
  calculate, based on the signal from the endoscope, a movement amount of the distal end of the insertion section of the endoscope;
  judge whether or not the movement amount of the distal end of the insertion section of the endoscope calculated is less than a predetermined threshold value;
  in response to judging that the movement amount of the distal end of the insertion section of the endoscope calculated is less than the predetermined threshold, judge that the differential classification operation is engaged; and
  in response to judging that the movement amount of the distal end of the insertion section of the endoscope calculated is not less than the predetermined threshold, judge that the differential classification operation is not engaged.

4. An image processing apparatus comprising:
a processor comprising hardware, wherein the processor is configured to:
  receive a plurality of images of a tissue including a lesion portion, the plurality of images being received from an endoscope operated by an operator;
  judge, based on a signal from the endoscope, whether or not to engage a differentiation classification operation to classify the lesion portion in one or more of the plurality of images;
  in response to judging that the differentiation classification operation is engaged,
    process the plurality of images to specify the lesion portion within the one or more of the plurality of images; and
    perform differentiation classification on the one or more images in which the lesion portion is specified to classify the lesion portion into at least one class of a plurality of classes; and
  in response to judging that the differentiation classification operation is not engaged, not process the plurality of images to specify the lesion portion within the one or more of the plurality of images, and
wherein the processor is configured to:
  judge, based on the plurality of images, whether or not the operator is gazing at a same region of the tissue; and
  in response to judging that the operator is gazing at the same region of the tissue, judge that the differentiation classification operation is engaged.

5. The image processing apparatus according to claim 4, wherein the processor is configured to:
  calculate a movement amount of one or more corresponding pixels in two or more of the plurality of images;
  judge whether or not the movement amount of the one or more corresponding pixels in the two or more of the plurality of images is within a predetermined area;
  in response to judging that the movement amount of the one or more corresponding pixels is within the predetermined area, judge that the operator is gazing at the same region of the tissue; and
  in response to judging that the movement amount of the one or more corresponding pixels is not within the predetermined area, judge that the operator is not gazing at the same region of the tissue.

6. An image processing apparatus comprising:
a processor comprising hardware, wherein the processor is configured to:
  receive a plurality of images of a tissue including a lesion portion, the plurality of images being received from an endoscope operated by an operator;

judge, based on a signal from the endoscope, whether or not to engage a differentiation classification operation to classify the lesion portion in one or more of the plurality of images;

in response to judging that the differentiation classification operation is engaged, process the plurality of images to specify the lesion portion within the one or more of the plurality of images; and perform differentiation classification on the one or more images in which the lesion portion is specified to classify the lesion portion into at least one class of a plurality of classes; and in response to judging that the differentiation classification operation is not engaged, not process the plurality of images to specify the lesion portion within the one or more of the plurality of images, and wherein the processor is configured to:

extract a blood vessel region of the tissue from one or more of the plurality of images;

calculate a size of the blood vessel region extracted;

judge whether the size of the blood vessel region is greater than a predetermined size;

in response to judging that the size of the blood vessel region is greater than the predetermined size, judge that the differentiation classification operation is engaged; and in response to judging that the size of the blood vessel region is not greater than the predetermined size, judge that the differentiation classification operation is not engaged.

7. An image processing apparatus comprising:

a processor comprising hardware, wherein the processor is configured to:

receive a plurality of images of a tissue including a lesion portion, the plurality of images being received from an endoscope operated by an operator;

judge, based on a signal from the endoscope, whether or not to engage a differentiation classification operation to classify the lesion portion in one or more of the plurality of images;

in response to judging that the differentiation classification operation is engaged, process the plurality of images to specify the lesion portion within the one or more of the plurality of images; and perform differentiation classification on the one or more images in which the lesion portion is specified to classify the lesion portion into at least one class of a plurality of classes; and in response to judging that the differentiation classification operation is not engaged, not process the plurality of images to specify the lesion portion within the one or more of the plurality of images, and wherein the processor is configured to:

determine, based on the signal from the endoscope, an observation state of the endoscope;

judge whether the observation state of the endoscope determined is a predetermined observation state;

in response to judging that the observation state of the endoscope determined is the predetermined observation state, judge that the differentiation classification operation is engaged; and in response to judging that the observation state of the endoscope determined is not the predetermined observation state, judge that the differentiation classification operation is not engaged.

8. The image processing apparatus according to claim 7, wherein the processor is configured to determine the observation state of the endoscope based on a setting operation signal of the observation state to the endoscope.

9. An image processing apparatus comprising:

a processor comprising hardware, wherein the processor is configured to:

receive a plurality of images of a tissue including a lesion portion, the plurality of images being received from an endoscope operated by an operator;

judge, based on a signal from the endoscope, whether or not to engage a differentiation classification operation to classify the lesion portion in one or more of the plurality of images;

in response to judging that the differentiation classification operation is engaged, process the plurality of images to specify the lesion portion within the one or more of the plurality of images; and perform differentiation classification on the one or more images in which the lesion portion is specified to classify the lesion portion into at least one class of a plurality of classes; and in response to judging that the differentiation classification operation is not engaged, not process the plurality of images to specify the lesion portion within the one or more of the plurality of images, and wherein the processor is configured to:

select, based on a differentiation operation signal received, one of a plurality of types of differentiation classification; and select one of a plurality of differentiation index to apply to performance of the differentiation classification based on the one of the plurality of types of differentiation classification selected.

10. The image processing apparatus according to claim 9, wherein the differentiation operation signal indicates one of:

a first set of one of more wavelength bands of light for normal observation is applied for pickup of the plurality of images of the tissue by the endoscope; and a second set of one or more wavelength bands of light for special observation is applied for pickup of the plurality of images of the tissue by the endoscope, and wherein the processor is configured to:

select, based on the differentiation operation signal indicating the first set of one or more wavelength bands of light is applied, a first type of differentiation classification; and select, based on the differentiation operation signal indicating the second set of one or more wavelength bands of light is applied, a second type of differentiation classification.

11. The image processing apparatus according to claim 9, wherein the differentiation operation signal indicates one of:

an enlargement observation operation is performed by the endoscope during pickup of the plurality of images of the tissue by the endoscope; and a proximity observation operation is performed by the endoscope during pickup of the plurality of images of the tissue by the endoscope, and wherein the processor is configured to:

select, based on the differentiation operation signal indicating the enlargement observation operation, a first type of differentiation classification; and select, based on the differentiation operation signal indicating the proximity observation operation, a second type of differentiation classification.

12. An image processing apparatus comprising:

a processor comprising hardware, wherein the processor is configured to:

receive a plurality of images of a tissue including a lesion portion, the plurality of images being received from an endoscope operated by an operator;

judge, based on a signal from the endoscope, whether or not to engage a differentiation classification operation to classify the lesion portion in one or more of the plurality of images;

in response to judging that the differentiation classification operation is engaged, process the plurality of images to specify the lesion portion within the one or more of the plurality of images; and perform differentiation classification on the one or more images in which the lesion portion is specified to classify the lesion portion into at least one class of a plurality of classes; and in response to judging that the differentiation classification operation is not engaged, not process the plurality of images to specify the lesion portion within the one or more of the plurality of images, and wherein the processor is configured to:

estimate a site, within an organ, at which the lesion portion specified is located; and perform differentiation classification to classify the lesion portion specified based on site estimated.

13. The image processing apparatus according to claim 12, wherein the processor is configured to:

estimate the site to be one of a rectum, a sigmoid colon, a descending colon, a transverse colon, an ascending colon, and a cecum when the organ is a large intestine;

estimate the site to be one of a cardia, a fundus ventriculi, a corpus ventriculi, an angulus ventriculi, an antrum, a pylorus, and a duodenum when the organ is a stomach;

estimate the site to be one of a jejunum and an ileum when the organ is a small intestine; and estimate the site to be one of a cervical esophagus, a thoracic esophagus, and an abdominal esophagus when the organ is an esophagus.

14. An image processing apparatus comprising:

a processor comprising hardware, wherein the processor is configured to:

receive a plurality of images of a tissue including a lesion portion, the plurality of images being received from an endoscope operated by an operator;

judge, based on a signal from the endoscope, whether or not to engage a differentiation classification operation to classify the lesion portion in one or more of the plurality of images;

in response to judging that the differentiation classification operation is engaged, process the plurality of images to specify the lesion portion within the one or more of the plurality of images; and perform differentiation classification on the one or more images in which the lesion portion is specified to classify the lesion portion into at least one class of a plurality of classes; and in response to judging that the differentiation classification operation is not engaged, not process the plurality of images to specify the lesion portion within the one or more of the plurality of images, and wherein the processor is configured to:

calculate a movement amount of a distal end of an insertion section of the endoscope; and change an amount of outputted support information depending on the movement amount calculated.

\* \* \* \* \*